United States Patent
Andersen et al.

(10) Patent No.: US 7,579,323 B1
(45) Date of Patent: Aug. 25, 2009

(54) HEMIASTERLIN ANALOGS

(75) Inventors: Raymond Andersen, Vancouver (CA); Edward Piers, Vancouver (CA); James Nieman, Kalamazoo, MI (US); John Coleman, Halifax (CA); Michel Roberge, Vancouver (CA)

(73) Assignee: The University of British Columbia, Vancouver, B.C. (CA)

( * ) Notice: Subject to any disclaimer, the term of this patent is extended or adjusted under 35 U.S.C. 154(b) by 0 days.

(21) Appl. No.: 09/581,511

(22) PCT Filed: Dec. 13, 1998

(86) PCT No.: PCT/CA98/01184

§ 371 (c)(1),
(2), (4) Date: Oct. 6, 2000

(87) PCT Pub. No.: WO99/32509

PCT Pub. Date: Jul. 1, 1999

(30) Foreign Application Priority Data

Dec. 19, 1997  (CA) .................................... 2225325

(51) Int. Cl.
*C07K 5/06* (2006.01)
(52) U.S. Cl. .......................... 514/19; 530/331
(58) Field of Classification Search ................. 530/330, 530/331; 514/18, 19
See application file for complete search history.

(56) References Cited

U.S. PATENT DOCUMENTS

| | | | |
|---|---|---|---|
| 4,048,305 A | 9/1977 | Molteni et al. | 424/177 |
| 5,661,175 A | 8/1997 | Kashman | 514/419 |
| 5,736,517 A | 4/1998 | Bogden | 514/14 |
| 6,126,939 A * | 10/2000 | Eisenbach-Schwartz et al. | 424/185.1 |
| 6,153,590 A | 11/2000 | Andersen et al. | 514/19 |
| 6,194,578 B1 | 2/2001 | Griffith et al. | |
| 6,214,799 B1 * | 4/2001 | Webber | 514/19 |
| 6,331,554 B1 * | 12/2001 | Dragovich | 514/357 |
| 6,362,166 B1 * | 3/2002 | Webber | 514/19 |

FOREIGN PATENT DOCUMENTS

| | | |
|---|---|---|
| EP | 0 150 227 | 8/1985 |
| EP | 1 002 802 | 12/2004 |
| NZ | 216551 | 9/1989 |
| NZ | 224706 | 7/1990 |
| WO | 96/33211 | 10/1996 |
| WO | 97/04004 | * 2/1997 |

OTHER PUBLICATIONS

Reetz, Angew. Chem., Int. Ed. Engl., 31(12), 1626-9, 1992).*
Falender (Biocatalysis and Biotransformation 13(2), 131-139, 1995.*
Chang, L. L. (Bioorganic & Medicinal Chemistry Letters 2(10), 1207-12, 1992).*
Baldwin, Jack E. (J. Chem. Soc., Chem. Comm. (16), 1280-1, 1986).*
Tetrahedron (1995), 51(39), 10653-62 CODEN; TETRAB; ISSN: 0040-4020, Sep. 25, 1995, Colman et al., "Cytotoxic peptides from the marine sponge Cymbastela sp."
Journal of Organic Chemistry, vol. 59, No. 11, Jun. 3, 1994, P. Crews et al, "Milnamide A., an Unusual Cytotoxic Tripeptide from the Marine Sponge Auletta cf. Constricta".
Journal of Organic Chemistry, vol. 52, No. 14, Jul. 10, 1987, pp. 3091-3093, Chan et al, "Stereostructures of Geodiamolides A and B, Novel Cyclodepsipeptides from the Marine Sponge Geodia s.p."
Experimental Hematology, vol. 23, No. 7, Jul. 1995, pp. 583-587, Fabian et al., "Growth modulation and differentiation af acute myeloid leukemia cells by jaspamide".
Talpir R. et al. Tetrahedron Lett. (1994) 35:4453-4456.
Anderson RJ. et al. Tetrahedron Letters (1997) 38(3):317-320.
Anderson HJ. et al. Cancer Chemother Pharmacol (1997) 39:223-226.
Coleman JE. et al. Acta Cryst. (1996) C51:1525-11527.
Evans D.A. et al. J. Am. Chem. Soc. (1990) 112:4011-4030.
Evans D.A. et al. Tetrahedron (1988) 44:5525-5540.
Frérot E. et al. Tetrahedron (1991) 47:259-270.
Hoffman A. J. Am. Chem. Soc. (1929) 51:2542-2547.
Dragovich, Peter S. et al., "Structure-Based Design, Synthesis, and Biological Evaluation of Irreversible Human Rhinovirus 3C Protease Inhibitors. 2. Peptide Structure—Activity Studies", *J. Med. Chem.* 41: 2819-2834 (1998).
Leftheris, Katerina, "Development of Highly Potent Inhibitors of Ras Farnesyltransferase Possessing Cellular and In Vivo Activity", *J. Med. Chem.* 39: 224-236 (1996).
Skehan, P. et al. New Colorimetric Cytotoxicity Assay for Anticancer-Drug Screening, Journal of National Cancer Institute vol. 82, No. 13, pp. 1107-1112, 1990.

* cited by examiner

*Primary Examiner*—David Lukton
(74) *Attorney, Agent, or Firm*—Arent Fox LLP

(57) ABSTRACT

This invention provides analogs of hemiasterlin, methods of synthesis of the analogs and use of the analogs as cytotoxic and anti-mitotic agents.

49 Claims, 7 Drawing Sheets

HEMIASTERLIN ANALOGS

This application is a 371 of PCT/CA98/01184, filed Dec. 18, 1998, which claims priority to CA 2,225,325, filed Dec. 19, 1997.

FIELD OF INVENTION

This invention relates to biologically active compounds and compositions, their use and derivation.

BACKGROUND

As described in Talpir, R. et al. (1994) Tetrahedron Lett. 35:4453-6 and in international patent application PCT/GB96/00942 published Oct. 24, 1996 under number WO96/33211, the compound hemiasterlin may be obtained from marine sponges or synthesized. As set forth in PCT/GB96/00942, hemiasterlin and the synthetic analogs described therein are cytotoxic and anti-mitotic.

Compounds that differ from hemiasterlin in the region of the indole moiety of hemiasterlin are novel. It has now been found that analogs of hemiasterlin wherein the indole moiety of hemiasterlin has been deleted or replaced demonstrate potent anti-mitotic and cytotoxic activity.

SUMMARY OF INVENTION

This invention provides a compound or pharmaceutically acceptable salt thereof, having the formula I

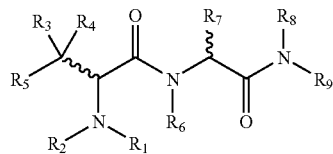

wherein, $R_1$ and $R_2$ are independently selected from the group consisting of: H, R, and ArR—, and where at least one of $R_1$ and $R_2$ is R and neither are ArR—, $R_1$ and $R_2$ together may optionally be a three to seven membered ring;

$R_3$ and $R_4$ are independently selected from the group consisting of: H, R, ArR—, and where at least one of $R_3$ and $R_4$ is R and neither are ArR— or Ar, $R_3$ and $R_4$ together may optionally be a three to seven membered ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ is:

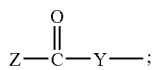

and wherein,

R is defined as a saturated or unsaturated moiety having a linear, branched, or cyclic skeleton containing one to ten carbon atoms, zero to four nitrogen atoms, zero to four oxygen atoms, and zero to four sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group;

X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;

Ar is defined as an aromatic ring selected from the group consisting of: phenyl, naphthyl, anthracyl, phenanthryl, furyl, pyrrolyl, thiophenyl, benzofuryl, benzothiophenyl, quinolyl, isoquinolyl, imidazolyl, thiazolyl, oxazolyl, and pyridyl, optionally substituted with R or X;

Y is defined as a moiety selected from the group consisting of: a linear, saturated or unsaturated, one to six carbon alkyl group, optionally substituted with R, ArR—, or X; and, Z is defined as a moiety selected from the group consisting of: —OH, —OR; —SH; —SR; —$NH_2$; —NHR; —$N(R)_2$; —NHCH($R_{11}$)COOH; and —NRCH($R_{11}$)COOH, wherein $R_{11}$ is a moiety having the formula: R, or —$(CH_2)_n NR_{12}R_{13}$, wherein n=1-4 and $R_{12}$ and $R_{13}$ are independently selected from the group consisting of: H; R; and —C(NH) ($NH_2$).

This invention also provide methods of preparing the aforementioned compound of formula I, and precursors thereof, as described herein.

This invention also provides the use of the aforementioned compound of formula I, or a pharmaceutically acceptable salt thereof, for:

(a) manufacture of a medicament;

(b) in a method whereby cells, including tumor cells, which are susceptible to the cytotoxic effects of the compound are treated with the compound or a pharmaceutically acceptable salt thereof; and (c) in a method whereby cells are treated with the compound or a pharmaceutically acceptable salt thereof, to bring about mitotic arrest in the cells, or the production of abnormal mitotic spindles in the cells.

DETAILED DESCRIPTION OF THE INVENTION

Figure 1:
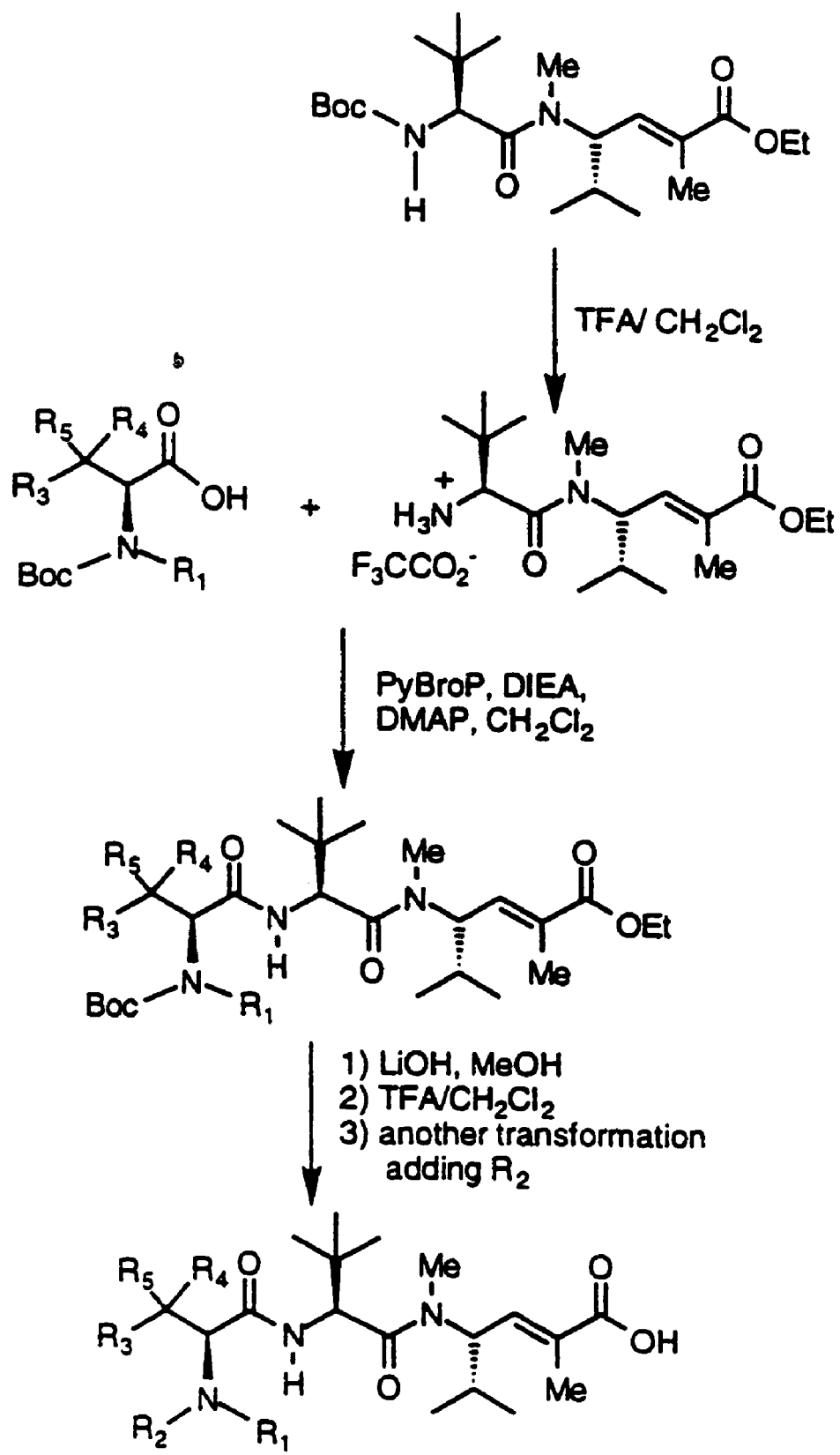
FIG. 1 is a schematic showing a preferred scheme for synthesis of a compound of this invention.

Except where otherwise stated, the recitation of a compound herein covers all possible salts of the compound, and denotes all possible isomers possible within the structural formula given for such compound, including geometrical and optical isomers. Unless otherwise stated, materials described herein comprising a compound for which isomers exist, are to be regarded as covering individual isomers, and, mixtures of isomers including racemic mixtures.

In the compound of formula I set out above, bonds drawn in wavy line are from carbon atoms which may be optical centers. Preferably, the following absolute configurations predominate:

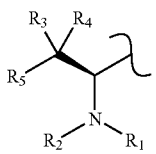 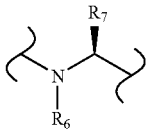

Except where otherwise stated, any moiety referred to herein which is described as "alkyl" will preferably be straight chain or, branched when possible, and will preferably have up to eight, more preferably up to six and even more preferably up to four carbon atoms. Except where otherwise stated optionally substituted alkyl groups are preferably unsubstituted. Methyl is the most preferred alkyl group.

In this specification, reference is made to alkyl moieties being saturated or unsaturated, thereby including within the definition of the moiety, alkene and alkyne groups (whether internal, terminal or part of a ring).

In a compound of formula I, the following substituents alone, or in combination, are preferred:

(a) $R_1$ and $R_2$ independently: H, methyl, ethyl, propyl, n-butyl, acetyl; or, where $R_1$ and $R_2$ are joined: cyclopropyl, cyclobutyl, cyclopentyl or cyclohexyl; more preferably $R_1$ and $R_2$ are independently: H or $CH_3$; most preferably $R_1$ is H and $R_2$ is $CH_3$;

(b) preferably no more than one of $R_3$ and $R_4$ is H; more preferably, $R_3$ and $R_4$ are independently: methyl, ethyl, n-propyl or n-butyl, or, where $R_3$ and $R_4$ are joined: β-cyclopropyl, β-cyclobutyl, β-cyclopentyl or β-cyclohexyl; most preferably $R_3$ and $R_4$ are each methyl;

(c) $R_5$: Ar in the definition of $R_5$ is preferably phenyl, naphthyl, anthracyl or pyrrolyl; preferably $R_5$ is phenyl, methyl or H; most preferably $R_5$ is phenyl or methyl;

(d) $R_6$ and $R_8$ independently: H or methyl, more preferably $R_6$ is H and $R_8$ is methyl;

(e) $R_7$: a three to six carbon, branched alkyl group; more preferably $R_7$ is —$C(CH_3)_3$; and (f) in $R_9$, Z is preferably OH, —$OR_{14}$ (wherein $R_{14}$ is a linear or branched one to six carbon alkyl group, —NHCH$(R)_{11})$COOH or —NCH$_3$CH$(R_{11})$COOH wherein $R_{11}$ is R, or —$(CH_2)_n$NHC(NH)(NH$_2$); or $R_9$ is preferably

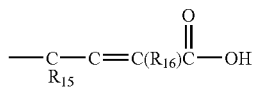

wherein $R_{15}$, is methyl, ethyl, n-propyl, isopropyl, tert-butyl, iso-butyl, or sec-butyl and $R_{16}$ is H, methyl, ethyl, propyl, iso-propyl, n-butyl, iso-butyl or sec-butyl; more preferably Z is OH and $R_9$ as a whole is:

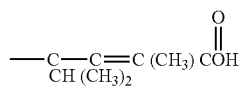

Where $R_9$ has a chiral center in moiety Y, the following absolute configuration is preferred, with reference to an example where the chiral center has a methyl substituent:

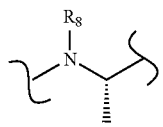

Compounds of formula I may be prepared by coupling moieties A, B and C as represented below using standard procedures, including procedures for coupling amino acids through a peptide bond.

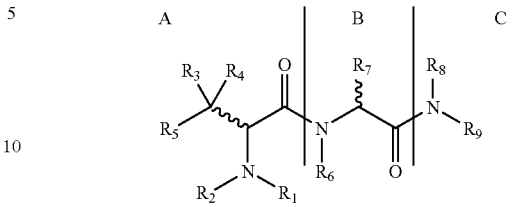

A coupling agent, for example PyBroP, is suitably used in the reaction. The reaction suitably comprises connecting amino acid moieties in the presence of the coupling agent, a base such as 4-dimethylaminopyridine and an organic solvent such as methylene chloride. Standard reaction quenching and purification procedures known in the art produce the coupled compound.

Preparation of moieties B and C as described above May be carried out using procedures and starting materials known in the art, for example by following the methods described in the aforementioned PCT/GB96/00942. The methods as set out in the examples herein may be employed, with suitable modification to materials and reagents, according to particular substituents of moieties A, B and C.

One aspect of this invention is a method for preparing a compound of formula I in which a compound of the formula:

II

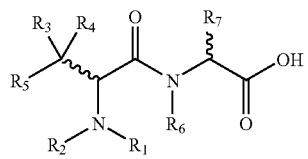

is coupled with a compound of the formula:

III

A compound of formula III may be prepared by known methods (such as described in PCT/GB96/00942) and by the method described in the examples herein.

A further aspect of this invention is a method for preparing a compound of the formula II described above in which a compound of the formula:

IV

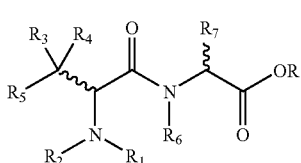

is treated with a base such as dilute sodium hydroxide in a solvent such as methanol for enough time to allow removal of OR; followed by acidification to about pH 3. Preferably R in formula IV is a simple alkyl chain, such as $CH_3$, and a protecting agent such as tert-butoxycarbonyl (Boc) may be used to protect the amine group; i.e. $R_1$ or $R_2$ is replaced by Boc. The Boc group is suitably removed by a reaction such as TFA/CH$_2$Cl$_2$ for about 1 hour at ambient temperatures. An appropriate isolation protocol produces the TFA salt. Subsequently another group (eg. $R_1$ or $R_2$) could be introduced on the nitrogen by standard techniques known to any person in the art, which produces compound of formula IV.

A further aspect of this invention is a method for preparing a compound of formula IV described above in which a compound of the formula:

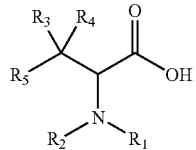

V is coupled with a compound of the formula:

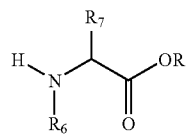

VI

Preparation of compound V can be accomplished by many procedures known to person skilled in the art. One such example is described below in FIG. 2. Compounds of formula VI may be prepared by methods known to persons of skill in the art.

A preferred method according to this invention for preparing a compound of formula I, is to prepare a dipeptide comprising moieties B and C and couple the dipeptide to moiety A. In this method, a compound of the following formula, wherein Q and T together are a combination of any two of the substituents: $R_1$, $R_2$ and a protecting group:

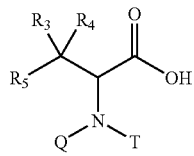

VII is coupled with a compound of the formula:

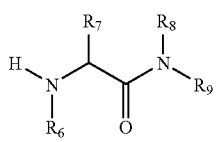

VIII

A compound of formula VIII may be prepared by coupling a compound of formula III as described above, with a compound of the formula:

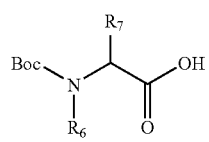

IX

Compounds of formula IX may be prepared by methods known to persons of skill in the art.

A further aspect of this invention is a method to prepare a compound of formula VII as described above in which a compound of the formula:

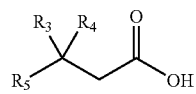

X is treated with a base followed by an azide compound. The azide derivative so produced is reduced to form an amine which is then treated with groups selected from: $R_1$, $R_1$ and Boc in the presence of a base such as sodium hydride.

FIG. 1 sets out a preferred scheme for preparation of a compound of formula I involving the coupling of amino acid moiety A with a dipeptide comprising moieties B and C. In the embodiment shown in the figure, the substituents of the dipeptide are those of hemiasterlin. The Boc protected dipeptide portrayed in the figure may be obtained by the methods set out in the examples herein. On the A moiety, Boc may replace $R_1$ rather than $R_2$ or both $R_1$ and $R_2$ may be present on the A moiety prior to coupling.

Figure 2:
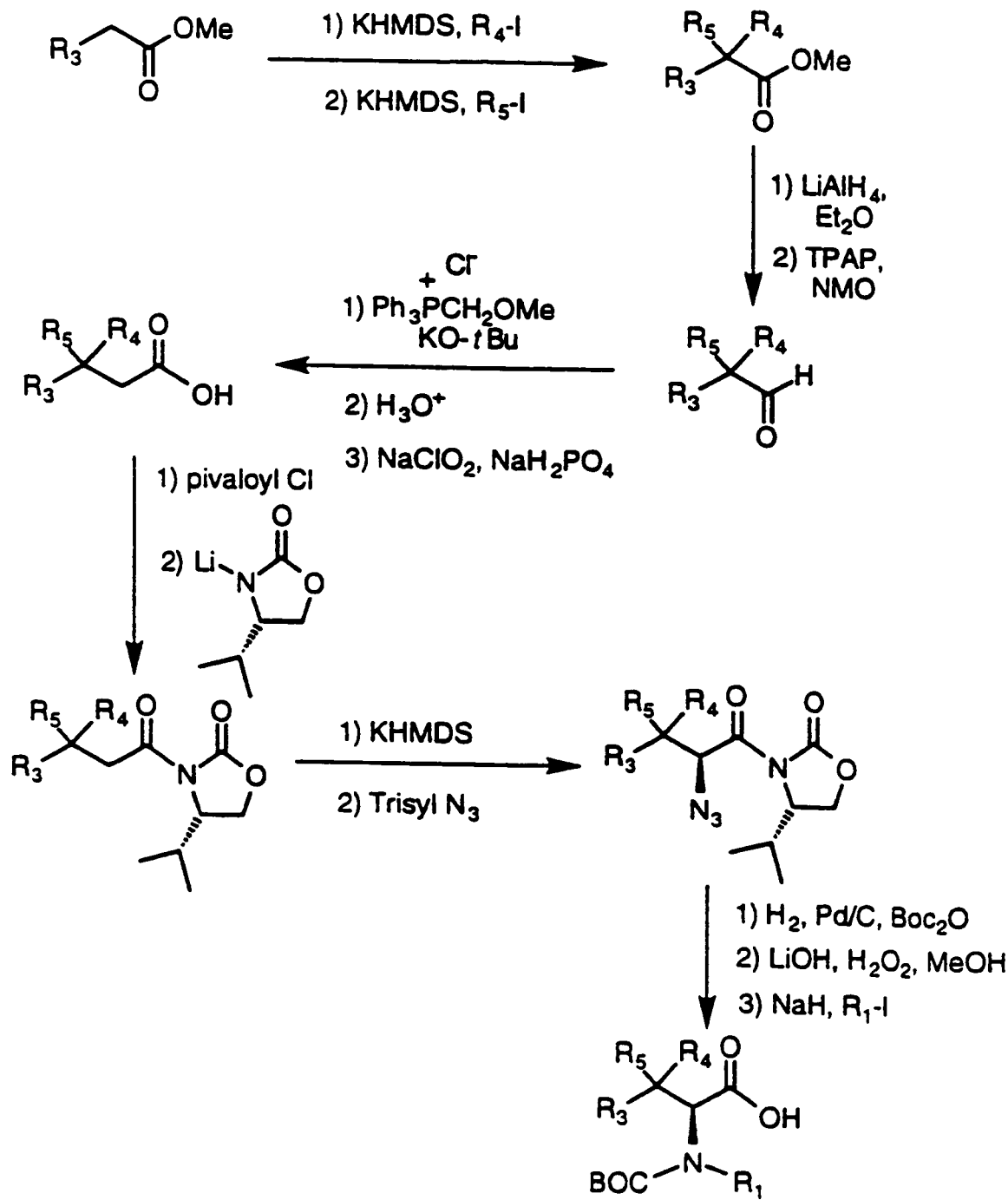
FIG. 2 is a schematic showing a preferred scheme for synthesis of the amino acid used in the coupling reaction shown in FIG. 1.

FIG. 2 sets out a preferred scheme for preparation of moiety A as used in the scheme shown in FIG. 1. $R_2$ may be added in place of Boc and Boc may replace $R_1$.

Compounds of formula I are biologically active. The invention includes the use of a compound of formula I. Compounds of formula I may have pesticidal, for example insecticidal activity. Preferably, however, the use is in the pharmaceutical field for medical or veterinarial applications.

The compounds described herein have utility as cytotoxic agents, particularly against tumor cells and may have utility as anti-bacterial or anti-viral agents. Therefore, this invention includes a pharmaceutical composition comprising an effective amount of a compound of formula I, in association with a carrier.

This invention further provides the use of a compound of formula I for the manufacture of a medicament for use in the treatment of cancer or a tumor in a mammal.

In using a compound of formula I for medical or veterinarial applications, the compound is preferably administered in a pharmaceutical composition comprising also a pharmaceutically acceptable carrier, and optionally, one or more other biologically active ingredients. Such compositions may be in any form used for administering pharmaceuticals, for example any form suitable for oral, topical, vaginal, intravenous, subcutaneous, parenteral, rectal and inhalatory application. The compositions may be provided in discrete dose units. The carriers may be particulate, with the compositions being, for example, tablets or powders, or liquid, with the compositions being, for example, oral syrups or injectable liquids, or aerosol, for inhalatory application.

For oral administration an excipient and/or binder may be present. Examples are sucrose, kaolin, glycerin, starch dextrins, sodium alginate, carboxymethylcellulose and ethyl cellulose. Colouring and/or flavouring agents may be present. A coating shell may be employed. For rectal administration oleaginous bases may be employed, for example lanolin or cocoa butter. For an injectable formulation buffers, stabilizers and isotonic agents may be included.

The dosage of a compound of formula I may depend upon the weight and physical condition of the patient; on the severity and longevity of the illness; and on the particular form of the active ingredient, the manner of administration and the composition employed. A daily dose of about 0.0001 to about 100 mg/kg of body weight taken singly or in separate doses of up to 6 times a day, or by a continuous infusion, embraces the effective amounts most typically required. A preferred range is about 0.001 to about 50 mg/kg of body weight, per day, most preferably about 0.01 to about 30 mg/kg of body weight, per day.

It is to be understood that use of a compound of formula I in chemotherapy can involve such a compound being bound to an agent, for example a monoclonal or polyclonal antibody, a protein or a liposome, which assists the delivery of the said compound to tumor cells.

This invention also includes the use of a compound of formula I as an antimitotic agent. Such use may be in procedures that require blocking cells in mitosis, such as the preparation of mitotic spreads for karyotype analysis. The compounds of this invention can also be used to probe microtubule function in mitotic cells.

EXAMPLES

Figure 3:
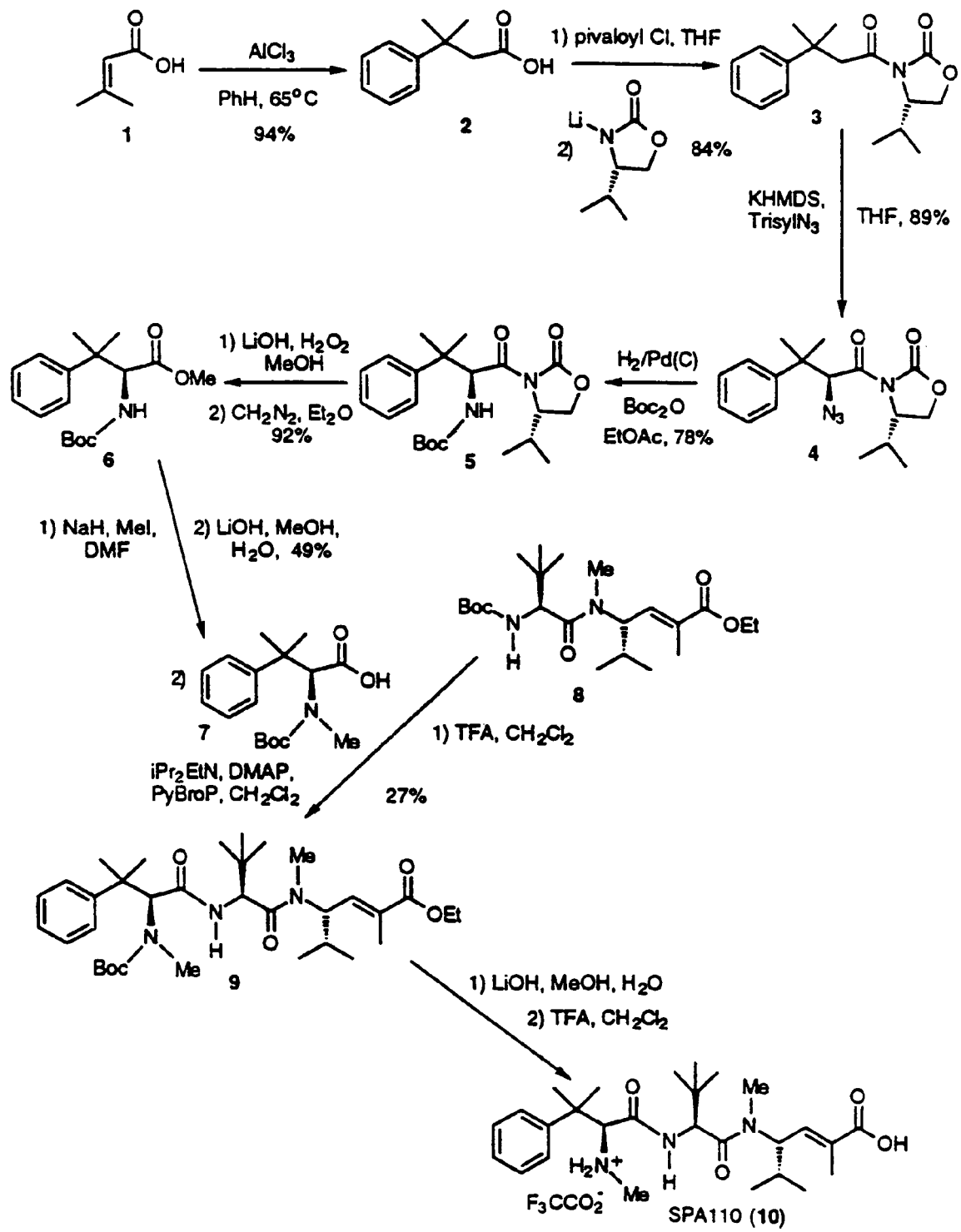
FIG. 3 is a schematic showing steps in the synthesis of a compound of this invention as described in the examples herein.
Figure 4:
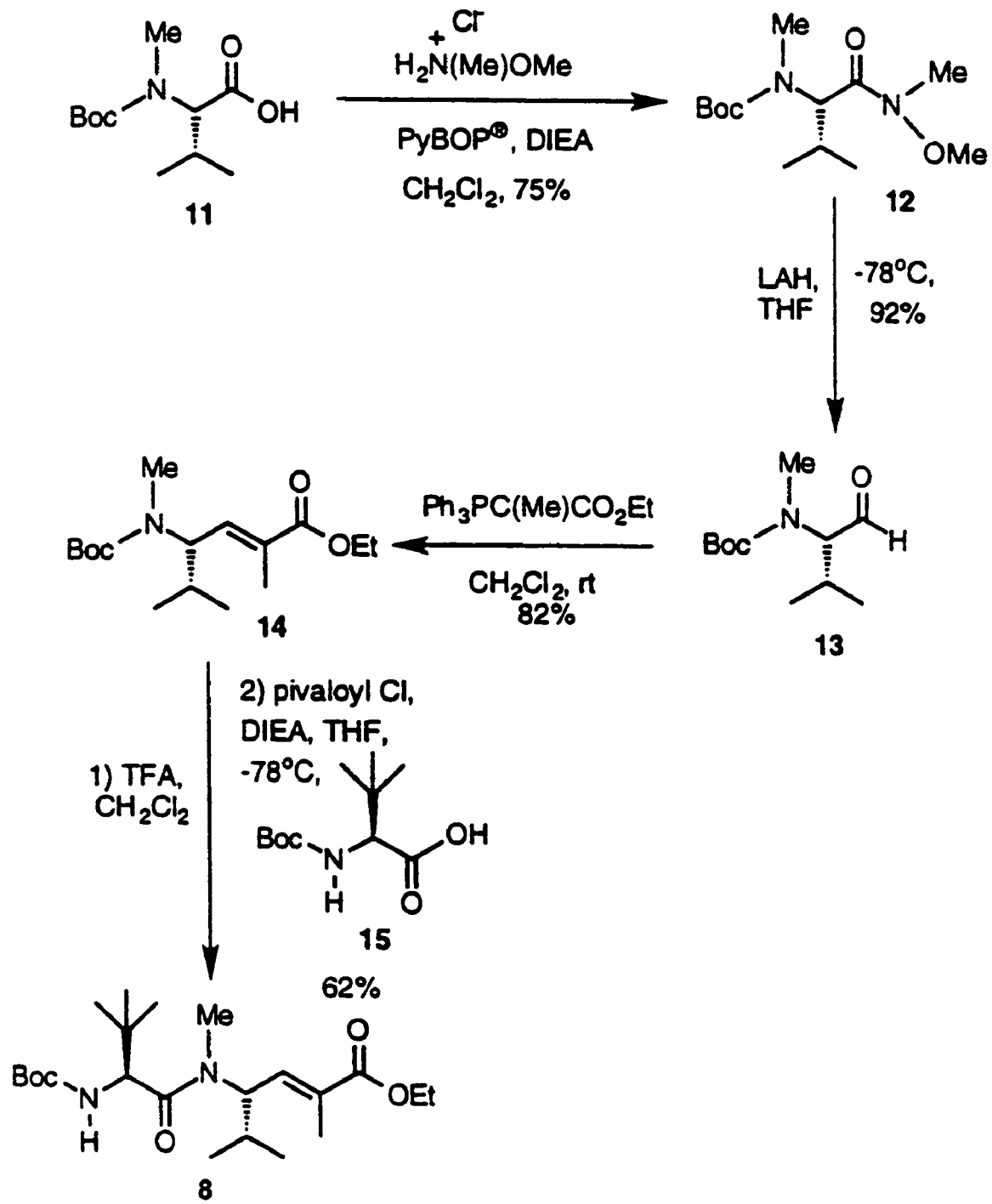
FIG. 4 is a schematic showing steps in the synthesis of the dipeptide shown in FIG. 3, as described in the examples herein.

The following examples provide a detailed description of preferred methods of synthesis of a preferred compound of this invention, SPA-110. Also described are precursor compounds and characterization of various compounds of this invention. FIGS. 3 and 4 schematically portray the synthesis of the a SPA-110 salt according to the examples. Reference numerals in the examples correspond to labelling of compounds in FIGS. 3 and 4 and labelling of compounds depicted in the examples.

3-methyl-3-phenylbutanoic acid (2)

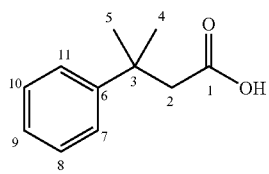

3-Methyl-2-butenoic acid (1, 5.10 g, 50.9 mmol) and $AlCl_3$ (20.4 g, 153 mmol) were placed in a one-neck round-bottomed flask. Benzene (50 mL) was added, which produced vigorous bubbling. Upon completion of the bubbling, a capped condenser (i.e. closed system) was attached, the reaction mixture was stirred and placed in an oil bath at 65° C. The pressure in the system was occasionally released. The progress of the reaction was followed by following the loss of starting material by GC. If the reaction was not complete within 1 h, a small quantity of $AlCl_3$ was added and stirring was continued. To the solution was added diethyl ether and the mixture was cooled to 0° C. Slowly conc. HCl and some water were added until all the solid dissolved and the pH was less than 2. The aqueous layer was extracted with diethyl ether three times. The organic layer was concentrated to 150 mL and then was extracted with a saturated sodium hydrogen carbonate solution six times. The combined aqueous layer were acidified with conc. HCl until the pH was less than 2. The acidic aqueous layer was extracted with diethyl ether three times and the accumulated organic layer was dried with magnesium sulfate. The solution was filtered and the diethyl ether was removed in vacuo producing a white solid (8.51 g, 47.7 mmol) in 94% yield, which did not need further purification. mp 55-56° C. $^1$H-NMR (400 MHz, $CDCl_3$) 10.45 (bs, 1H, $CO_2H$), 7.38 (d, 2H, J=7.2 Hz, H-11 and H-7), 7.32 (t, 2H, J=7.2 Hz, H-10 and H-8), 7.21 (t, 2H, J=7.2 Hz, H-9), 2.65 (s, 2H, H-2), 1.47 (s, 6H, H-5 and H-4); Mass spectrum (EI) 178 (23, M.$^+$), 119 (100, $[C_9H_{11}]^+$). For pioneering work to form 2 see: F. J. Eijkman (1908) Chem. Kentr. II, p. 110; or A. Hoffman (1929) J. Am. Chem. Soc. 51:2542.

(4S)-3-(3-methyl-3-phenyl-1-oxobutyl)-4-isopropyl-2-oxazolidinone (3)

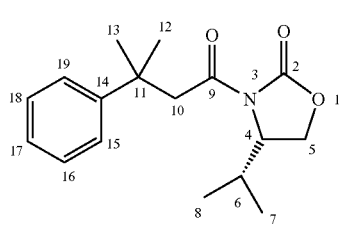

3-Methyl-3-phenylbutanoic acid (2, 1.00 g, 5.61 mmol) was dissolved in 70 mL of THF and cooled to -78° C. Triethylamine (1.17 mL, 8.42 mmol) and trimethylacetyl chloride (0.760 mL, 6.17 mmol) were added to the reaction flask producing a white solid. The resulting mixture was warmed to 0° C. for 1 h and then cooled back down to -78° C. In a second flask butyllithium (6.84 mL, 1.6 M in hexanes, 10.9 mmol) was added dropwise with vigorous stirring to a solution of (4S)-(-)-4-isopropyl-2-oxazolidinone (1.45 g, 11.2 mmol) at -78° C. in THF (60 mL) producing a white precipitate. The resulting suspension of the lithiated oxazolidinone was added via cannula to the reaction flask. Stirring was continued for 2 h, water was added and the reaction mixture was warmed to room temperature, whereupon it was extracted three times with diethyl ether. The combined organic extracts were dried over magnesium sulfate, and concentrated in vacuo. The product was purified by radial chromatography (4 mm plate, 3:7 diethyl ether-pet. ether) affording compound 3 as a clear, colourless oil in 84% yield (1.37 g, 4.74 mmol). $^1$H-NMR (400 MHz, $CDCl_3$) 7.38 (d, 2H, J=7.3 Hz, H-19 and H-15) 7.28 (t, 2H, J=7.3 Hz, H-18 and H-16), 7.16 (t, 1H, J=7.3 Hz, H-17), 4.22-4.18 (m, 1H, H-4), 4.05 (dd, 1H, J=9.0 and 2.8 Hz, 1H-5), 4.00 (t, 1H, J=9.0 Hz, 1H-5), 3.38-3.30 (m, 2H, H-10), 2.16-2.12 (m, 1H, H-6), 1.48 (s, 3H, H-13 or H-12), 1.47 (s, 3H, H-13 or H-12), 0.79 (d, 3H, J=7.1 Hz, H-8 or H-7), 0.71 (d, 3H, J=6.9 Hz, H-8 or H-7); Mass spectrum (EI) 289 (8, M.$^+$), 119 (100, $[C_9H_{11}]^+$). Optical rotation obtained was $[\alpha]_D^{25}$ +69.5 (c 1.16, $CHCl_3$). Compound 3 was prepared according to D. A. Evans et al. (1988) Tetrahedron 44:5525.

Preparation of the 4-isopropyl-2-oxazolidinone 4

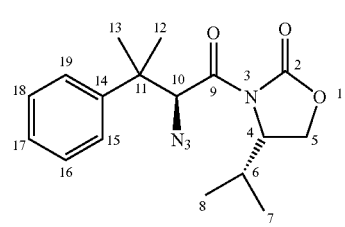

Oxazolidinone 3 (472 mg, 1.63 mmol), dried under high vacuum for 0.5 h, was dissolved in THF and cooled to -78° C. (10 mL). Freshly titrated potassium bis(trimethylsilyl)amide (15.6 mL, 0.115 M in THF, 1.79 mmol) was added and the resulting solution was stirred at -78° C. for 1 h. A solution of 2,4,6-triisopropylbenzenesulfonyl azide (625 mg, 2.04 mmol) in THF (5 mL) at -78° C. was added via cannula and after 2 min. the orange coloured reaction mixture was treated with glacial acetic acid (0.429 mL, 7.50 mmol), warmed to 40° C. in a water bath and stirred for a further hour. To the light yellow mixture was added brine (35 mL), water (35 mL) and the aqueous phase was extracted three times with 80 mL diethyl ether. The combined organic extracts were washed with a saturated sodium hydrogen carbonate solution (20 mL), dried with magnesium sulfate and concentrated in vacuo. The product was purified by radial chromatography (4 mm plate, 3:7 diethyl ether-pet. ether, sample was loaded with diethyl ether) affording azide 5 as a colourless oil (482 mg, 1.46 mmol) in 89% yield. $^1$H-NMR (400 MHz, CDCl$_3$) 7.39 (d, 2H, J=7.2 Hz, H-19 and H-15), 7.31 (t, 2H, J=7.2 Hz, H-18 and H-16), 7.23 (t, 1H, J=7.2 Hz, H-17), 5.64 (s, 1H, H-10), 3.95 (dd, 1H, J=8.7 and 2.2 Hz, 1H-5), 3.89°-3.85 (m, 1H, H-4), 3.56 (t, 1H, J=8.7 Hz, 1H-5), 2.31-2.26 (m, 1H, H-6), 1.54, 1.52 (s, 3H, H-13 and H-12), 0.83 (d, 3H, J=7.0 Hz, H-8 or H-7), 0.79 (d, 3H, J=6.9 Hz, H-8 or H-7); Mass spectrum (DCI, NH$_3$) 349 (45, [M+NH$_5$]$^+$), 348 (100, [M+NH$_4$]$^+$), 331 (12, [M+H]$^+$), 303 (57, [M—N$_2$]$^+$), 119 (94, [C$_9$H$_{11}$]$^+$). Optical rotation obtained was $[\alpha]_D^{25}$ +121.5 (c 1.1, CHCl$_3$). Compound 4 was prepared according to the methodology developed by D. A. Evans et al. (1990) J. Am. Chem. Soc. 112: 4011. 2,4,6-Triisopropylbenzenesulfonyl azide was prepared by the method of O. C. Dermer et al. (1955) J. Am. Chem. Soc. 77:70.

Preparation of the 4-isopropyl-2-oxazolidinone 5

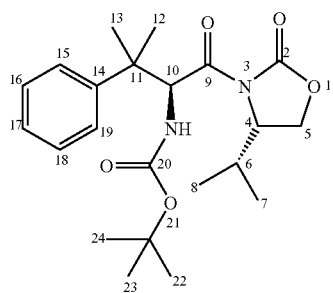

Azide 4 (418 mg, 1.26 mmol), 10% palladium on charcoal (280 mg), and di-tert-butyl dicarbonate (608 mg, 2.78 mmol) were placed in a 100 mL flask. Ethyl acetate (37 mL) was added and the resulting black suspension was stirred at room temperature. The mixture was flushed with argon, then with hydrogen and was stirred under a hydrogen balloon overnight (~14 h). The reaction mixture was filtered through silica gel and the collected material was washed with ethyl acetate. The combined filtrate was concentrated in vacuo and the crude mixture was purified by flash column chromatography (3:7 diethyl ether-pet. ether) to afford compound 5, a viscous colourless oil, in 78% yield (400 mg, 0.989 mmol). $^1$H-NMR (400 MHz CDCl$_3$) 7.40 (d, 2H, J=7.4 Hz, H-19 and H-15), 7.29 (t, 2H, J=7.4 Hz, H-18 and H-16), 7.21 (t, 1H, J=7.4 Hz. H-17), 6.12 (d, 1H, J=9.9 Hz, H-10), 5.11 (bs, 1H, N—H), 3.89 (d, 1H, J=8.4 and 1.9 Hz. H-5), 3.82-3.79 (m, 1H, H-4), 3.45 (t, 1H, J=8.4 Hz, H-5), 2.26-2.22 (m, 1H, H-6), 1.41 (s, 9H, H-24, H-23 and H-22), 0.80 (d, 3H, J=7.0 Hz, H-8 or H-7), 0.76 (d, 3H, J=6.9 Hz, H-8 or H-7); Mass spectrum (DCI, CH$_4$/NH$_3$ mix) 405 (1, [M+H]$^+$), 349 (7, [M—C$_4$H$_9$]$^+$), 230 (100, [C$_9$H$_{14}$N$_2$O$_5$]$^+$). Optical rotation obtained was $[\alpha]_D^{24}$ +118.4 (c 0.935, CHCl$_3$). Compound 5 was prepared according to the methodology developed by D. A. Evans et al. (1990) (supra).

Methyl (2S)-2-(tert-butyloxycarbonyl)amino-3-methyl-3-phenylbutanoate (6)

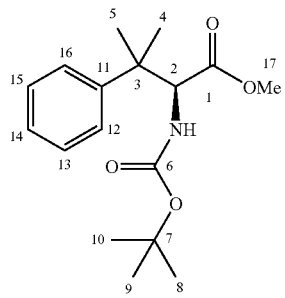

Oxazolidinone 5 (245 mg, 0.605 mmol) was dissolved in a mixture of 7.1 mL THF and 1.8 mL water. This solution was cooled to 0° C. and hydrogen peroxide (0.618 mL, 30% aqueous, 5.45 mmol) and lithium hydroxide (1.82 mL, 1.0 M, 1.82 mmol) were added. The resulting mixture was stirred at room temperature overnight (~15 h). The excess peroxide was quenched by addition of sodium hydrogen sulfite (7.1 mL, 1.5 M, 10.7 mmol) and stirring was continued for 1 h. The aqueous phase was acidified with 1.0 M citric acid and the mixture was extracted three times with ethyl acetate. The combined ethyl acetate extracts were dried over magnesium sulfate and concentrated in vacuo. To the remaining crude material was added a solution of diazomethane in diethyl ether until the solution stayed yellow. After bubbling argon through the solution for 15 min., the remaining volatile components were removed in vacuo to afford crude compound 6. Purification of ester 6 was accomplished by radial chromatography (2 mm plate, 3:7 diethyl ether-pet. ether, sample was loaded with CHCl$_3$), producing a clear colourless oil (171 mg, 0.555) in 92% yield. $^1$H-NMR (400 MHz, CDCl$_3$) 7.33-7.27 (m, 4H, H-16, H-15, H-13, H-12), 7.20 (t, 1H, J=6.7 Hz, H-14), 4.99 (bd, 1H, J=8.8 Hz, H-2), 4.50 (bd, 1H, J=8.8 Hz, N—H), 3.48 (s, 3H, H-17), 1.41, 1.38 (s, 3H, H-5 and H-4), 1.37 (s, 9H, H-10,H-9, and H-8); Mass spectrum (EI) 307 (0.1, M.$^+$), 234 (2, [M-Ot-Bu]$^+$), 119 (100, [C$_9$H$_{11}$]$^+$). Optical rotation obtained was $[\alpha]^{25}$ +35.2 (c 2.98, CHCl$_3$). Compound 5 was prepared according to the methodology developed by D. A. Evans et al. (1990) (supra).

(2S)-N-tert-butoxycarbonyl-N-methyl-3-methyl-3-phenylbutanoic acid (7)

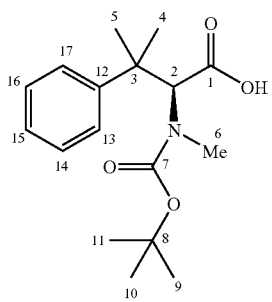

To a vigorously stirred solution of ester 6 (43.4 mg, 0.141 mmol) in 2 mL dry DMF were added sodium hydride (10.2 mg, 4.24 mmol) followed by methyl iodide (0.088 mL, 1.41 mmol) and the resulting grey suspension was stirred overnight (~20 h) at room temperature. The excess sodium hydride was quenched by cautious addition of water and the mixture was acidified by dropwise addition of 1.0 M citric acid. The acidic mixture was extracted three times with ethyl acetate, the combined organic layer extracted three times with brine, dried over magnesium sulfate and concentrated in vacuo. The resulting light orange oil was dissolved in 4 mL methanol in a 25 mL flask. To the solution was added 1.0 mL of water, followed by 1.13 mL of 1.0 M lithium hydroxide. The reaction mixture was heated at 60° C. overnight (~14 h), producing a white precipitate. To the resultant mixture was added saturated sodium hydrogen carbonate solution and water; the mixture was then extracted with ethyl acetate. The aqueous layer was acidified with 1.0 M citric acid until the pH was ~4. The mixture was extracted three times with ethyl acetate. The combined organic layers were dried with magnesium sulfate and concentrated in vacuo. Compound 7 was also found in the first ethyl acetate extraction so it was also added to the crude product. Purification of acid 7 was performed by silica gel column chromatography (1:2 diethyl ether-pet. ether with 1% acetic acid) resulting in a 49% yield (21.2 mg, 0.0670 mmol) of a clear colourless oil. $^1$H-NMR (400 MHz, CDCl$_3$) 7.41 (d, 1.3H, J=7.6 Hz, H-17 and H-13), 7.37 (d, 1.3H, J=7.6 Hz, H-17 and H-13), 7.28 (t, 2H, J=7.6 Hz, H-16 and H-14), 7.18 (t, 1H, J=7.2 Hz, H-15), 5.17 (bs, 0.66H, H-2), 4.93 (bs, 0.33H, H-2), 2.75 (s, 1.05H, H-6), 2.62 (s, 1.95H, H-6), 1.55 (s, 3H, H-5 or H-4), 1.49-1.39 (m, 12H, H-5 or H-4 and H-11, H-10 and H-9); Mass spectrum (EI) 307 (0.1, M.$^+$), 234 (3, [M-Ot-Bu]$^+$), 119 (100, [C$_9$H$_{11}$]$^+$), 57 (78, [C$_4$H$_9$]$^+$); Exact mass calc d for C$_{17}$H$_{25}$NO$_4$: 307.1783. Found (EI): 307.1793.

Preparation of Compound 9

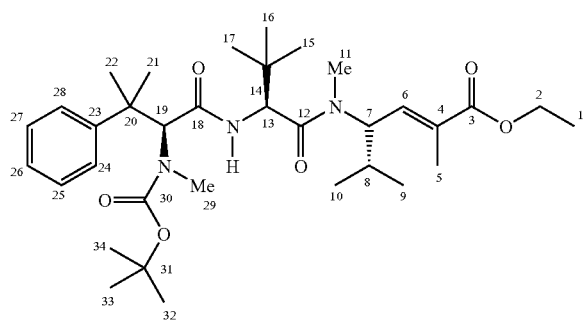

9

The N-Boc-amino ester 8 (71.6 mg, 0.174 mmol) was dissolved in 1 mL, CH$_2$Cl$_2$ and 1 mL of TFA was added. The reaction mixture was stirred at room temperature for 0.5 h. Removal of the solvent in vacuo, followed by repeated rinsing of the remaining material with CH$_2$Cl$_2$ (3×5 mL) and evaporation of the residual solvent afforded the TFA salt of the amino acid ester 8. In a separate flask, to a solution (or suspension) of the N-Boc protected amino acid 7 (51.5 mg, 0.167 mmol) in 0.5 mL CH$_2$Cl$_2$, was added DIEA (0.0875 mL, 0503 mmol), DMAP (0.031 mg, 0.10 mmol) and PyBroP (0.0781 mg, 0.167 mmol). The solution was stirred for a few minutes and then a solution of the TFA salt of 8 was added in 1 mL of CH$_2$Cl$_2$ via cannula addition. The reaction mixture was stirred at room temperature for 18 h. To the mixture was added water, CH$_2$Cl$_2$ and ten drops of 10% aqueous HCl. The resulting biphasic solution was extracted with CH$_2$Cl$_2$ (three times with 20 mL). The organic layer was extracted with saturated aqueous sodium hydrogen carbonate (10 mL), dried with magnesium sulfate and the solvent was removed in vacuo. The product was purified by flash chromatography (silica gel, 1:1 diethyl ether-pet. ether) affording the protected tripeptide 9 as a clear colourless oil in 27% yield (0.0272 g, 0.0454 mmol). $^1$H-NMR (400 MHz, CDCl$_3$) 7.84 (bd, 1H, J=9.5 Hz, N—H), 7.4--7.30 (m, 5H, H-28, H-27, H-25, H-24), 7.21 (bt, 1H, J=7.2 Hz, H-26), 6.63 (bd, 1H, J=9.6 Hz, H-6), 5.08 (t, 1H, J=9.6 Hz, H-7), 4.83 (d, 1H, J=9.5 Hz, H-13), 4.17 (q, 2H, J=7.1 Hz, H-2), 3.02 (s, 3H, H-11), 2.15 (s, 0.66H, H-29), 2.02 (s, 2.37H, H-29), 1.94-1.81 (m, 1H, H-8), 1.88 (s, 3H, H-5), 1.39-1.38 (m, 9H, H-34, H-33 and H-32), 1.28 (t, 3H, J=7.1 Hz, H-1), 0.98 (s, 9H, H-17, H-16 and H-15), 0.83, 0.77 (d, 3H, J=6.6 Hz, H-10 and H-9); PyBroP is described in E. Frérot et al. (1991) Tetrahedron 47:259.

SPA 110-trifluoroacetate salt (10)

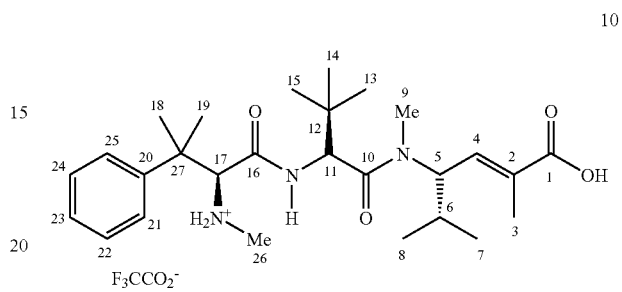

10

To a solution of the ethyl ester 9 (23.0 mg, 0.0382 mmol) in 1.1 mL MeOH was added 0.30 mL water and 0.31 mL of a 1.0 M aqueous solution of lithium hydroxide (0.31 mmol). The reaction mixture was stirred at room temperature overnight (~20 h) whereupon it was acidified by dropwise addition of 1.0 M citric acid and then extracted three times with ethyl acetate. The combined organic extracts were dried with magnesium sulfate and concentrated in vacuo. Under an argon atmosphere, the crude oil was dissolved in 1 mL CH$_2$Cl$_2$ and the solution was treated with TFA (1 mL) and then was stirred at room temperature for 0.5 h. Removal of the excess solvents in vacuo, followed by rinsing of the remaining material three times with CH$_2$Cl$_2$ (5 mL) and evaporation of the residual solvent, produced the TFA salt. HPLC purification of the crude product using a Magnum reverse phase C-18 column (H$_2$O(45): MeOH(55) with 0.05% TFA) afforded the tripeptide 10 as a white powder. $^1$H-NMR (400 MHz, CD$_3$OD) 7.53 (d, 2H, J=7.6, H-25 and H-21), 7.44 (t, 2H, J=7.6 Hz, H-24 and H-22), 7.34 (t, 1H, J=7.6 Hz, H-23), 6.76 (d, 1H, J=9.1 Hz, H-4), 5.04 (t, 1H, J=10.1 Hz, H-5), 4.91, 4.34 (s, 1H, H-17 and H-11), 3.13 (s, 3H, H-9), 2.49 (H-26), 2.08-1.99 (m, 1H, H-6), 1.90 (s, 3H, H-3), 1.46, 1.37 (s, 3H, H-19 and H-18), 1.05 (s, 9H, H-15, H-14 and H-13), 0.89 (d, 3H, J=6.1 Hz, H-8 or H-7), 0.88 (d, 3H, J=6.5 Hz, H-8 or H-7); Mass spectrum (EI) 474 (0.1, [M—CF$_3$CO$_2^-$]$^+$), 458 (0.1, [M-16-CF$_3$CO$_2^-$]$^+$), 382 (2), 162 (62), 69 (74), 45(100).

Nα-Boc-Nα-methyl-l-valine
N-methoxy-N-methylamide (12)

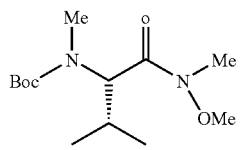

12

To a cold (0° C.) solution of N-Boc-N-methylvaline (11) (5.0 g, 21.6 mmol), N,O-dimethylhydroxylamine hydrochloride (2.8 g, 28 mmol), and PyBOP® (11.2 g, 22 mmol) in CH$_2$Cl$_2$ (22 mL) was added DIEA (8.4 mL, 75 mmol). After 1 min., the reaction mixture was warmed to room temperature and stirring was continued for 1 h. If the pH value of the mixture was less than 7, the mixture could be treated with a few drops DIEA to allow the reaction to go to completion. The mixture was poured into 200 mL of diethyl ether and the resultant mixture was washed successively with 3 N hydrochloric acid (3×30 mL), saturated aqueous sodium hydrogen carbonate solution (3×30 mL), and saturated aqueous sodium chloride (3×30 mL). The organic layer was dried with magnesium sulfate and the solvent was evaporated, followed by chromatography of the crude product (silica gel, 1:3 diethyl ether-pet. ether), afforded 12 (4.46 g, 75% yield) as a colourless oil. $^1$H-NMR (200 MHz, CDCl$_3$): 0.84 (d, J=6.6 Hz, 4H, (CH$_3$)$_2$), 0.85 (d, J=6.6 Hz, 2H, (CH$_3$)$_2$), 1.41 (s, 6H, Boc-(CH$_3$)$_3$), 1.44 (s, 3H, Boc-(CH$_3$)$_3$), 2.15-2.30 (m, 1H, CH), 2.75 (s, 1H, NCH$_3$), 2.78 (s, 2H, NCH$_3$), 3.10 (bs, 3H, NCH$_3$), 3.64 (s, 1H, OCH$_3$), 3.68 (s, 2H, OCH$_3$), 4.66 (d, J=10 Hz, 0.4H, CH), 4.95 (d, J=10 Hz, 0.6H, CH); Exact mass calc'd for C$_{13}$H$_{27}$N$_2$O$_4$ (M+H)$^+$: 275.19708. Found (DCI): 275.19710. Optical rotation obtained was $[\alpha]^{25}$ +128.3 (c 2.9, CHCl$_3$).

N-Boc-N-methyl-l-valinal (13)

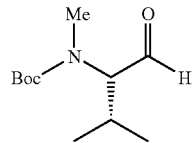

Lithium aluminum hydride (875 mg, 23 mmol) was added to a solution of Nα-Boc-Nα-methyl-L-valine N-methoxy-N-methylamide (12) (2.0 g, 7.7 mmol) in dry THF (8 mL) and the reaction mixture was stirred for 20 min. The mixture was poured into a stirring solution of potassium hydrogen sulfate (3.14 g, 23 mmol) in water (100 mL). Diethyl ether (75 mL) was added, the layers separated and the aqueous layer extracted with diethyl ether (3×50 mL). The organic layers were combined, and washed sequentially with 3 N hydrochloric acid (3×30 mL), saturated aqueous sodium hydrogen carbonate (3×30 mL), and saturated aqueous sodium chloride (3×30 mL). The organic layer was dried with magnesium sulfate and the solvent was evaporated to yield the crude aldehyde 13 (1.52 g, 92% yield). Aldehyde 13 was used without further purification. Note: 13 can be stored under argon for ~2 weeks, but when stored in organic solvents at room temperature, undergoes slow decomposition. $^1$H-NMR (200 MHz, CDCl$_3$) 0.73 (d, J=6.9 Hz, 3H, CH$_3$), 0.91 (d, J=6.9 Hz, 3H, CH$_3$), 1.27 (s, 9H, Boc-(CH$_3$)$_3$), 2.02-2.15 (m, 1H, CH), 2.63 (s, 2H, NCH$_3$), 2.72 (s, 1H, NCH$_3$), 3.44 (d, J=9.5 Hz, 0.5H, CH), 3.86 (d, J=9 Hz, 0.5H, CH), 9.45 (s, 1H, CH); Exact mass calc'd for C$_{11}$H$_{22}$NO$_3$ (M+H)$^+$: 216.15997; Found (DCI): 216.15996; Optical rotation obtained was $[\alpha]_D^{25}$ −104.2 (c 5.5, CHCl$_3$).

Ethyl (2E,4S)-N-Boc-N-methyl-4-amino-2,5-dimethylhex-2-enoate (14)

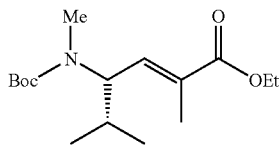

To a solution of aldehyde 13 (1.75 g, 8.7 mmol) in dry CH$_2$Cl$_2$ (9.0 mL) under an argon atmosphere at room temperature was added (carbethoxyethylidene)triphenylphosphorane (4.19 g, 11.3 mmol) and stirring was continued for a 4 h. The reaction mixture was diluted with water (100 mL) and extracted with diethyl ether (3×100 mL). The combined organic extracts were washed with saturated aqueous sodium chloride (100 mL), dried with magnesium sulfate and concentrated in vacuo. The crude oil was purified by flash chromatography (silica gel, 2:23 diethyl ether-pet. ether) to afford the required E-2-alkenoate 14 as a colourless oil (2.13 g, 82% yield). $^1$H-NMR (200 MHz, CDCl$_3$) 0.74 (d, J=6 Hz, 3H, CH$_3$), 0.79 (d, J=6 Hz, 3H, CH$_3$), 1.17 (t, J=0.7 Hz, 3H, CH$_3$), 1.34 (s, 9H, Boc-(CH$_3$)$_3$), 1.72 (m, 1H, CH), 1.78 (s, 3H, —CH$_3$), 2.60 (bs, 3H, NCH$_3$), 4.08 (q, J=7 Hz, 2H, CH$_2$), 4.15-4.20 (m, 0.5H, CH), 4.21-4.32 (m, 0.5H, CH), 6.54 (d, J=8 Hz, 1H, CH); Exact mass calc'd for C$_{16}$H$_{30}$N0$_4$ (M+H)$^+$: 300.21750; Found (DCI): 300.21754. Optical rotation obtained was $[\alpha]_D^{25}$ +61.1 (c 9.1, CHCl$_3$).

General Procedure 1: Trifluoacetic Acid Mediated Cleavage of N-Boc Groups

N-Boc-amino acid ester (1.0 equiv.) was treated with TFA/CH$_2$Cl$_2$ (0.1 mmol/1 mL) at room temperature for 0.5 h. Removal of the solvent in vacuo, followed by repeated rinsing of the residual material with CH$_2$Cl$_2$ (3×5 mL) and evaporation of the remaining traces of solvent afforded the TFA salt of the amino acid ester in quantitative yield. TFA salts were used without further purification.

General Procedure 2: Trimethylacetyl Chloride-Mediated Peptide Coupling

To a cold (−78 C) stirred solution of acid (1.1 equiv.) in dry THF (1 mL/mmol) under an argon atmosphere was added DIEA (1.5 equiv.) and trimethylacetyl chloride (1.2 equiv.). The resulting mixture was warmed to 0° C. for 1 h and then re-cooled to −78 C. DIEA (2.2 equiv.) was added via cannula to the reaction flask followed by the addition via cannula of the TFA salt of the amino acid ester (1.0 equiv., prepared by general procedure 1) in dry THF (0.5 mL/mmol) at −78 C. Stirring was continued for 1 h and water (40 mL) was added. The mixture was allowed to warm to room temperature, and extracted with diethyl ether (3×50 mL). The combined organic extracts were washed with saturated aqueous sodium chloride (50 mL), dried over magnesium sulfate, and concentrated in vacuo. The crude oil was purified by flash chromatography (silica gel, diethyl ether-pet. ether) to afford the desired dipeptide as a colourless oil.

Dipeptide 8

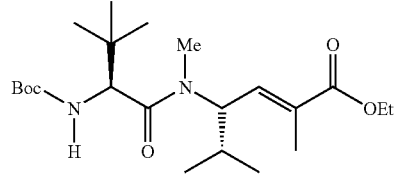

Following general procedure 2, dipeptide 8 was prepared with the following quantities of reagents and solvents: N-Boc-tert-leucine (15), 156 mg (0.52 mmol); trimethylacetyl chloride, 64 mL (0.52 mmol); DIEA, 99 mL (0.57 mmol); N-Boc-MHVV-OEt (14), 110 mg (0.47 mmol): DIEA, 198 mL (1.14 mmol); THF, 7 mL. Purification of the crude product by flash chromatography (silica gel, 1:5 diethyl ether-pet. ether) afforded 121 mg of 8 (62% yield). $^1$H-NMR (200 MHz, CDCl$_3$) 0.76 (d, J=6 Hz, 3H, CH$_3$), 0.80 (d, J=6 Hz, 3H, CH$_3$), 0.88 (s, 9H, (CH$_3$)$_3$), 1.22 (t, J=7 Hz, 3H, CH$_3$), 1.33 (s, 9H, Boc-(CH$_3$)$_3$), 1.79-1.89 (m, 1H, CH), 1.83 (s, 3H, CH$_3$), 2.91 (s, 3H, NCH$_3$), 4.12 (q. J=7 Hz, 2H, CH$_2$), 4.35 (d, J=10 Hz, 1H, CH), 5.03 (t, J=10 Hz, 1H, CH), 5.14 (d, J=10 Hz, 1H, NH), 6.57 (d, J=8 Hz, 1H, CH); Exact mass calcd for C$_{22}$H$_{41}$N$_2$O$_5$ (M+H)$^+$: 413.30154; Found (DCI): 413.30119. Optical rotation obtained was $[\alpha]_D^{25}$ −76.9 (c 2.43, CHCl$_3$).

Assay for Cytotoxicity

Figure 5A:
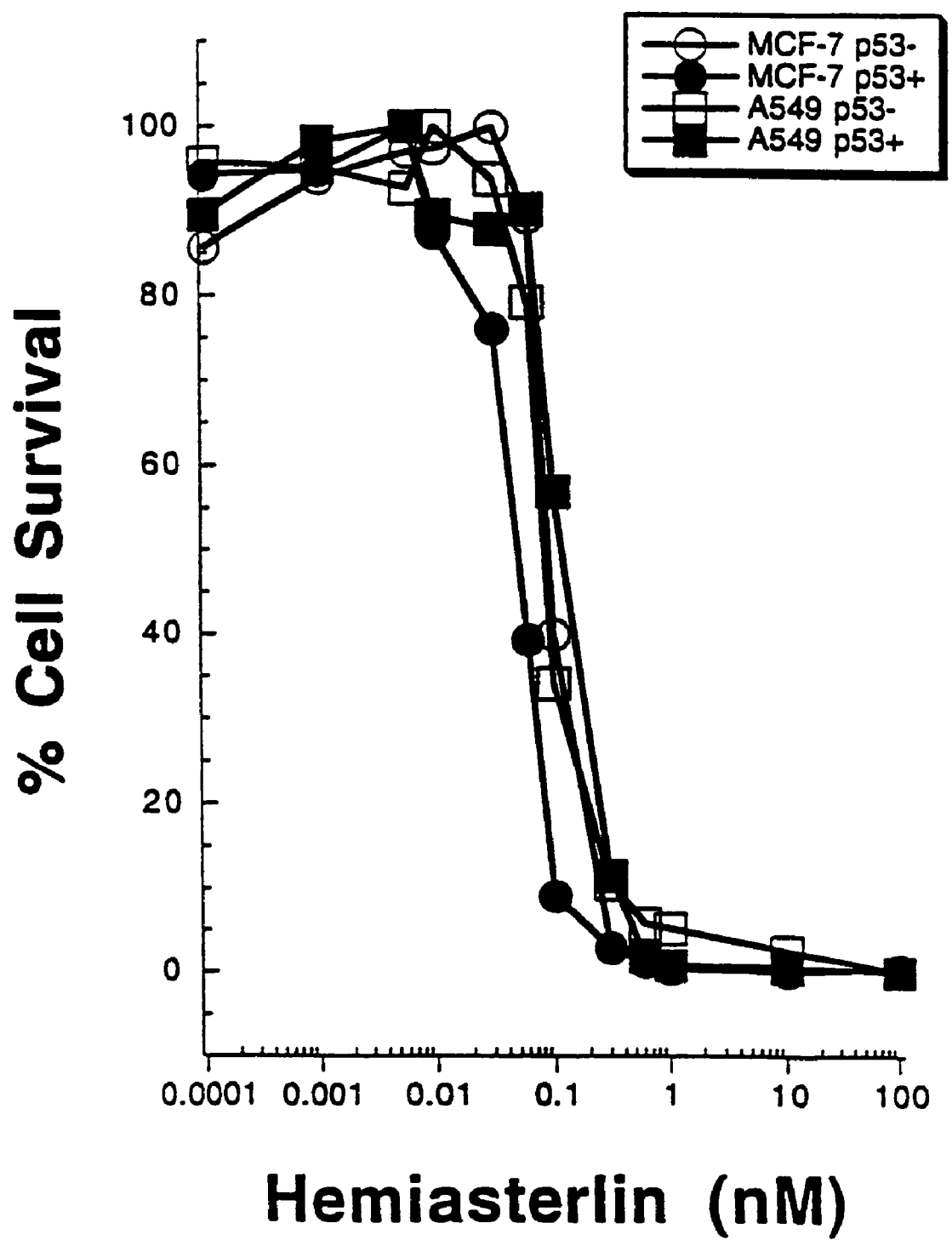
FIGS. 5A and 5B are graphs comparing the cytoxicity of hemiasterlin to SPA-110, as described in the examples herein.
Figure 5B:
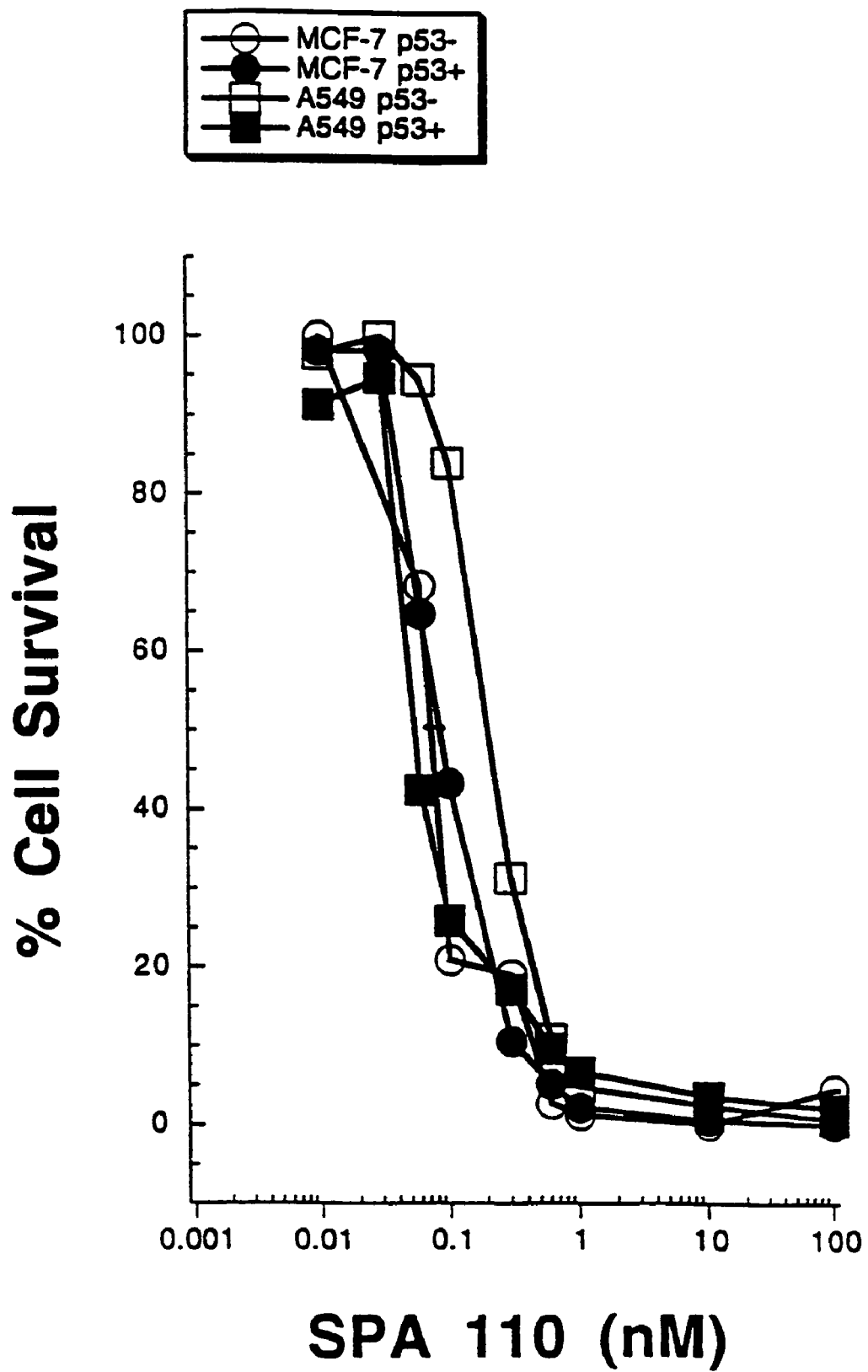

Cytotoxicity of SPA-110 compared to hemiasterlin as against p53+ and p53− variants of human breast cancer MCF-7 cells and A549 tumor cells was determined according to the methods described in J. Immunol. Methods 65:55-63 (1983). Results shown in FIGS. 5A and 5B show that SPA-110 is more cytotoxic in some instances than the naturally occurring compound.

Assay for Antimitotic Activity

Antimitotic activity is detected by enzyme-linked immunosorbent assay using a mitosis-specific antibody, TG-3 (from Albert Einstein College of Yeshiva University, Bronx, N.Y.; and see: PCT application published Jul. 4, 1996 under WO96/20218).

MCF-7 mp 53⁻ cells (expressing a dominant-negative p53 mutation as described in S. Fan, et al. (1955) Cancer Research 55:1649-1654) were cultured as monolayers in DMEM supplemented with 10% fetal bovine serum, 2 mM L-glutamine, 50 units/ml penicillin, 50 µg/ml streptomycin, 1 mM sodium pyruvate, MEM non-essential amino acids, 1 µg/ml bovine insulin, 1 µg/ml hydrocortisone, 1 ng/ml human epidermal growth factor, and 1 ng/ml β-estradiol at 37° C. in humidified 5% $CO_2$. The cells were seeded at 10,000 cells per well of 96-well polystyrene tissue culture plates (Falcon) in a volume of 200 µl cell culture medium. The cells were allowed to grow for 24 hours and compounds were added at about 1 µg/ml or 10 µg/ml (from 1000-fold stocks in dimethylsulfoxide) and the cells were incubated for 20 hours. Nocodazole (Sigma) served as a positive control. After treatment with the agent to be tested, the cell culture medium was removed completely and the 96-well tissue culture plates were frozen at −70° C. for up to 2 hours. The frozen cells were thawed by addition of 100 µl of ice-cold lysis buffer (0.5 mM phenylmethylsulfonylfluoride, 1 mM ethylene glycol-bis(β-aminoethyl ether) N,N,N,N'-tetraacetic acid, pH 7.4,) and lysed by pipeting up-and-down 10 times. The cell lysates were transferred to 96-well PolySorp ELISA plates (Nunc) and dried completely by blowing warm air at about 37° C. with a hair drier positioned about 3 feet above the plates. Protein binding sites were blocked by adding 200 µl per well of 10 mM Tris HCl pH 7.4, 150 mM NaCl, 0.1 mM PMSF, 3% (w/v) dried non-fat milk (Carnation) for 1 hour at room temperature. This was removed and replaced with 100 µl of the same solution containing 0.1-0.15 µg/ml TG-3 mitosis-specific monoclonal antibody and horseradish peroxidase-labelled goat anti-mouse IgM (1021-05, Southern Biotechnology Associates) at a dilution of 1/500. After overnight incubation at 4° C., the antibody solution was removed and the wells were rinsed 3 times with 200 µl rinse buffer (10 mM Tris HCl pH 7.4, 0.02% Tween 20). 100 µl of 120 mM $Na_2HPO_{41}$ 100 mM citric acid, pH 4.0 containing 0.5 mg/ml 2,2'-azino-bis(3-ethylbenzthiazoline-6-sulfonic acid) and 0.01% hydrogen peroxide was added for 1 hour at room temperature and the plates were read at 405 nm using a BioTek plate reader.

Figure 6:
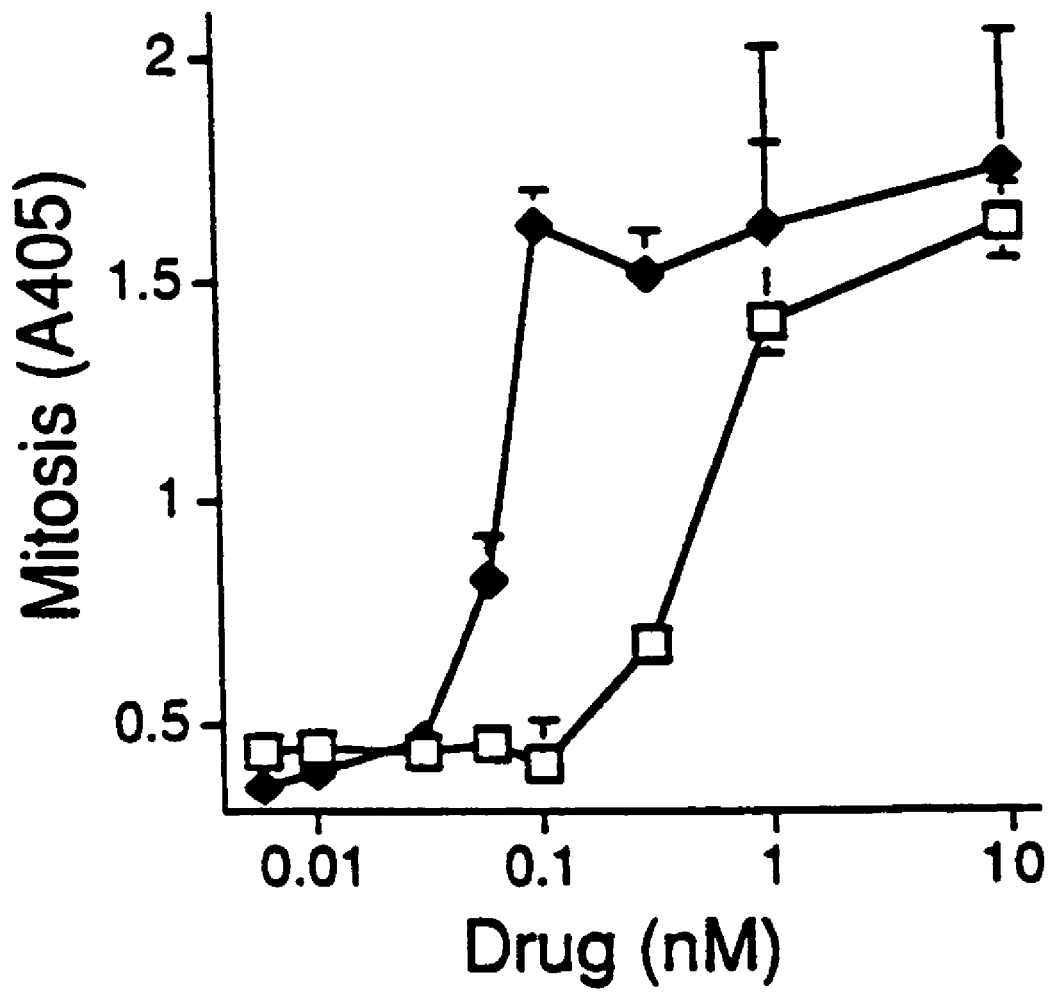
FIG. 6 is a graph comparing the anti-mitotic activity of SPA-110 (♦) to hemiasterlin (□), as described in the examples herein.

Results comparing antimitotic activity of hemiasterlin to SPA-110 are shown in FIG. 6. SPA-110 exhibited considerably greater antimitotic activity than the naturally occurring compound.

In Vivo Activity of SPA-110

The compound SPA-110 was evaluated in vivo using standard pharmacological test procedures which measure its ability to inhibit the growth of human tumor xenografts. The human colon carcinoma LOVO (American Type Culture Collection, Rockville, Md. #CCL-229) was grown in tissue culture in RPMI supplemented with 10% FBS. Athymic nu/nu female mice (Charles River, Wilmington, Mass.) were injected sub-cutaneously in the flank area with $7.0 \times 10^6$ LOVO cells. When tumors attained a mass of between 80 and 120 mg, the mice were randomized into treatment groups (day zero). Animals were treated intravenously once a day on days 1, 5, and 9 post staging (day zero) with 1 mg/kg/dose of SPA-110 prepared in 2.5% ethanol in saline or with saline as the vehicle control. Some animals were treated intraperitonealy once a day on days 1, 5 and 9 post staging with 1 mg/kg/dose Vincristine as a positive control. Tumor mass was determined every 7 days [(length×width²)/2] for 28 days post staging. RTG or relative tumor growth (Mean tumor mass on days 7, 14, 21 and 28 divided by the mean tumor mass on day zero) was determined for each treatment group. % T/C was calculated as RTC (treated group) % RTC (vehicle control group)×100. Statistical analysis (Student-t-test) of log relative tumor growth was used to compare treated verses control group in each experiment. A p-value (p≦0.05), which indicates a statistically significant reduction in relative tumor growth, was obtained in each case. 5 of 5 animals treated at day 28 with SPA-110 survived. 9 of 10 animals treated at day 28 with vincristine survived. The results are shown in the following table.

| Treatment | % T/C day 7 | % T/C day 14 | % T/C day 21 | % T/C day 28 |
|---|---|---|---|---|
| Vincristine | 34 | 37 | 44 | 47 |
| SPA-110 1 mg/kg | 16 | 18 | 30 | 47 |

Relative Activity of Compounds of this Invention

Various analogs of SPA-110 have been synthesized and characterized for their cytotoxic and anti-mitotic activities. The high degree of correlation between cytotoxicity and anti-mitotic capacity indicates that the cytotoxicity of the compounds of this invention is due to the compounds' anti-mitotic activity. The following structures are analogs falling within the scope of this invention depicted in approximately descending order of cytotoxic/anti-mitotic activity.

| Compound Name | Compound structure (TFA salt) Me=$CH_3$ |
|---|---|
| SPA110 | 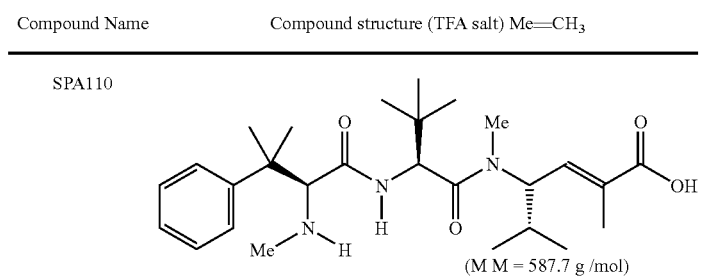 (M M = 587.7 g /mol) |

-continued

| Compound Name | Compound structure (TFA salt) Me=CH₃ |
|---|---|
| SPA115 | 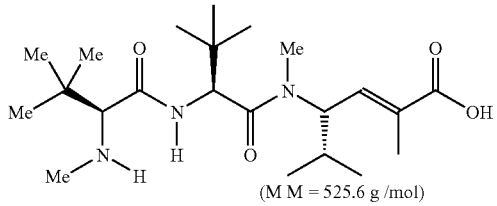<br>(M M = 525.6 g /mol) |
| SPA123 | 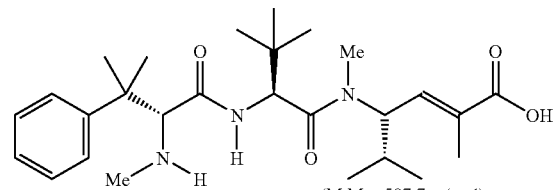<br>(M M = 587.7 g /mol) |
| SPA116 | 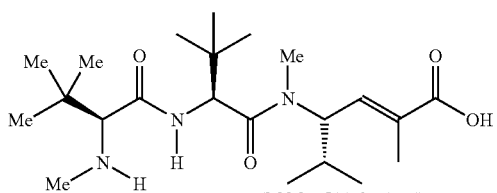<br>(M M = 511.6 g /mol) |
| SPA121 | 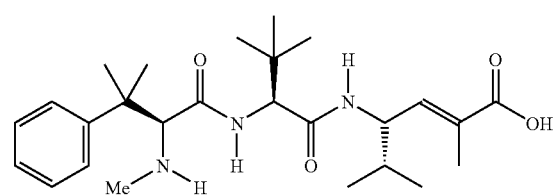<br>(M M = 573.7 g /mol) |
| SPA122 | 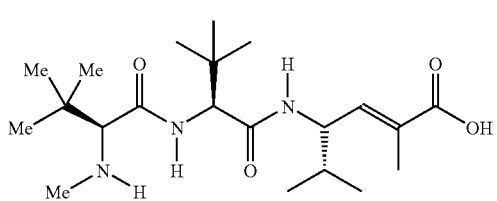<br>(M M = 511.6 g /mol) |
| SPA114 | 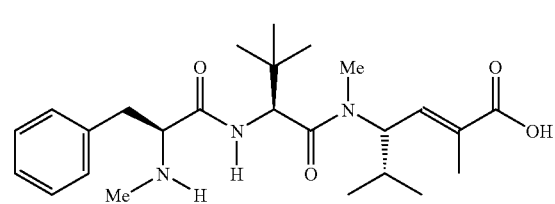<br>(M M = 559.6 g /mol) |

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the claims herein, which substance includes obvious chemical equivalents of the compounds and methods set out in the claims.

We claim:

1. A compound or pharmaceutically acceptable salt thereof, of the formula:

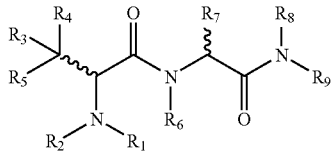

wherein:

$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —$CO_2$H, —CHO, —COSH, or —$NO_2$;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—;

and $R_9$ is:

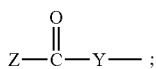

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2$H, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3$H, —$SOR_{10}$, —$SO_2R_{10}$, wherein $R_{10}$ is a linear, branched or cyclic, one to ten carbon saturated or unsaturated alkyl group, the ring formed by joining $R_3$ and $R_4$ is a three to seven member non-aromatic cyclic skeleton within the definition of R, Ar is an aromatic ring selected from the group consisting of: phenyl, naphthyl, anthracyl, and pyrrolyl;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl;

X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2$H, —$CO_2R$, —CHO, —COR, —$CONH_2$, —CONHR, —$CON(R)_2$, —COSH, —COSR, —$NO_2$, —$SO_3$H, —SOR, and —$SO_2R$; and Z is defined as a moiety selected from the group consisting of: —OH, —OR; —SH; —SR; —$NH_2$; —$NRCH(R_{11})$COOH; and —$NHCH(R_{11})$COOH, wherein $R_{11}$ is a moiety having the formula: R, or —$(CH_2)_nNR_{12}R_{13}$, wherein n=1-4 and $R_{12}$ and $R_{13}$ are independently selected from the group consisting of: H; R; and —C(NH)($NH_2$), or pharmaceutically acceptable salt thereof.

2. A compound or pharmaceutically acceptable salt thereof, of the formula:

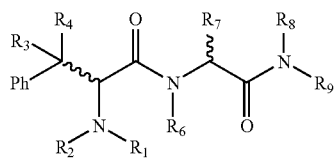

wherein:

$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —$CO_2$H, —CHO, —COSH, or —$NO_2$;

$R_3$ and $R_4$ are independently selected from the group consisting of: H, R, and ArR—, or $R_3$ and $R_4$ are joined to form a ring;

$R_6$ is selected from the group consisting of: H, R, and ArR—;

$R_7$ and $R_8$ are independently selected from the group consisting of: H, R, and ArR—;

and $R_9$ is:

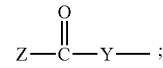

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2$H, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3$H, —$SOR_{10}$, —$SO_2R_{10}$, wherein $R_{10}$ is a linear, branched or cyclic, one to ten carbon saturated or unsaturated alkyl group, the ring formed by joining $R_3$ and $R_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

3. A compound or pharmaceutically acceptable salt thereof, of the formula:

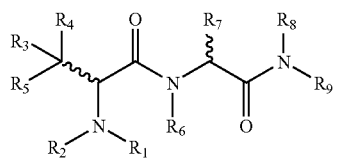

I wherein:

R$_1$ and R$_2$ are independently selected from the group consisting of: H, R, and ArR—, provided that neither R$_1$ or R$_2$ is tert-butoxycarbonyl, or R$_1$ and R$_2$ are joined to form a ring, or provided that where one of R$_1$ or R$_2$ is H, the other is not benzoyl;

R$_3$ and R$_4$ are independently selected from the group consisting of: methyl, ethyl, n-propyl and n-butyl;

R$_5$ is selected from the group consisting of: H, R, ArR—, and Ar;

R$_6$ is selected from the group consisting of: H, R, and ArR—;

R$_7$ and R$_8$ are independently selected from the group consisting of: H, R, and ArR—; and R$_9$ is:

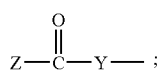

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_1$ and R$_2$ or by joining R$_3$ and R$_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

4. The compound of claim 3, wherein R$_3$ and R$_4$ are each —CH$_3$.

5. The compound of claim 4, wherein R$_5$ is Ar.

6. A compound or pharmaceutically acceptable salt thereof, of the formula:

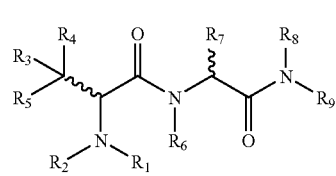

I wherein:

R$_1$ and R$_2$ are independently selected from the group consisting of: H, R, and ArR—, provided that neither R$_1$ or R$_2$ is tert-butoxycarbonyl, or R$_1$ and R$_2$ are joined to form a ring;

R$_3$ and R$_4$ are joined and form a moiety selected from the group consisting of cyclopropyl, cyclobutyl, cyclopentyl and cyclohexyl;

R$_5$ is selected from the group consisting of: H, R, ArR—, and Ar;

R$_6$ is selected from the group consisting of: H, R, and ArR—;

R$_7$ and R$_8$ are independently selected from the group consisting of: H, R, and ArR—; and $R_9$ is:

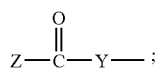

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_1$ and R$_2$ or by joining R$_3$ and R$_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

7. A compound or pharmaceutically acceptable salt thereof, of the formula:

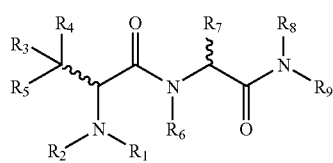

I wherein:
R$_1$ and R$_2$ are independently selected from the group consisting of H, methyl, ethyl, propyl, n-butyl and acetyl;
R$_3$ and R$_4$ are independently selected from the group consisting of: H, R, and ArR—, or R$_3$ and R$_4$ are joined to form a ring;

R$_5$ is selected from the group consisting of: H, R, ArR—, and Ar;

R$_6$ is selected from the group consisting of: H, R, and ArR—;

R$_7$ and R$_8$ are independently selected from the group consisting of: H, R, and ArR—;

provided that if either one of R$_1$ and R$_2$ is H, then each of R$_3$, R$_4$, R$_6$ and R$_8$ are H and R$_5$ is isopropyl or phenyl, and R$_7$ is methyl or benzyl;

and

R$_9$ is:

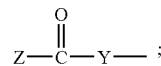

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, —S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_1$, is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

8. A compound or pharmaceutically acceptable salt thereof, of the formula:

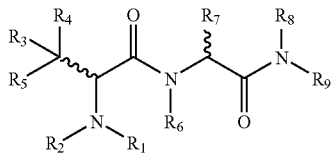

wherein:
R$_1$ and R$_2$ are alkyl and are joined to form a cyclic moiety which together with the N atom, consists of 3, 4, 5, or 6 members;
R$_3$ and R$_4$ are independently selected from the group consisting of: H, R, and ArR—, or R$_3$ and R$_4$ are joined to form a ring;
R$_5$ is selected from the group consisting of: H, R, ArR—, and Ar;
R$_6$ is selected from the group consisting of: H, R, and ArR—;
R$_7$ and R$_8$ are independently selected from the group consisting of: H, R, and ArR—;
and
R$_9$ is:

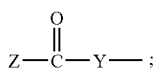

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_1$ and R$_2$ or by joining R$_3$ and R$_4$ is a three to seven member non-aromatic cyclic skeleton within the definition of R,
Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;
X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;
Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and
Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

9. A compound or pharmaceutically acceptable salt thereof, of the formula:

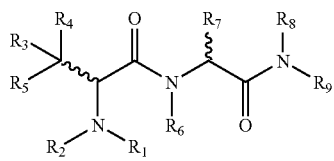

wherein:
R$_1$ and R$_2$ are independently H, CH$_3$ or acetyl;
R$_3$ and R$_4$ are independently selected from the group consisting of: H, R, and ArR—, or R$_3$ and R$_4$ are joined to form a ring;
R$_5$ is selected from the group consisting of: H, R, ArR—, and Ar;
R$_6$ is selected from the group consisting of: H, R, and ArR—;
R$_7$ and R$_8$ are independently selected from the group consisting of: H, R, and ArR—; provided that if either one of R$_1$ and R$_2$ is H, then each of R$_3$, R$_4$, R$_6$ and R$_8$ are H and R$_5$ is isopropyl or phenyl, and R$_7$ is methyl or benzyl;
and
R$_9$ is:

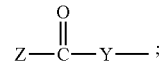

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R,
Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;
X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH($R_{11}$)COOH; and —NHCH($R_{11}$)COOH, wherein $R_{11}$ is a moiety having the formula: R, or —(CH$_2$)$_n$NR$_{12}$R$_{13}$, wherein n=1-4 and $R_{12}$ and $R_{13}$ are independently selected from the group consisting of: H; R; and —C(NH)(NH$_2$), or pharmaceutically acceptable salt thereof.

10. A compound or pharmaceutically acceptable salt thereof, of the formula:

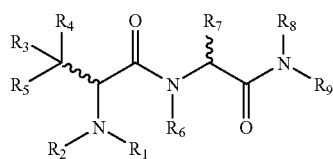

wherein:

$R_1$ and $R_2$ are independently H or $CH_3$;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; provided that if either one of $R_1$ and $R_2$ is H, then each of $R_3$, $R_4$, $R_6$ and $R_8$ are H and $R_5$ is isopropyl or phenyl, and $R_7$ is methyl or benzyl; and $R_9$ is:

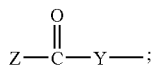

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_3$ and $R_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH($R_{11}$)COOH; and —NHCH($R_{11}$)COOH, wherein $R_{11}$ is a moiety having the formula: R, or —(CH$_2$)$_n$NR$_{12}$R$_{13}$, wherein n=1-4 and $R_{12}$ and $R_{13}$ are independently selected from the group consisting of: H; R; and —C(NH)(NH$_2$), or pharmaceutically acceptable salt thereof.

11. The compound of claim 10, wherein $R_1$ is H, and $R_2$ is —CH$_3$.

12. The compound of claim 10, wherein $R_5$ is Ar.

13. The compound of claim 10, wherein $R_3$ and $R_4$ are each —CH$_3$.

14. The compound of claim 13, wherein $R_5$ is Ar.

15. The compound of claim 14, wherein $R_5$ is phenyl.

16. A compound or pharmaceutically acceptable salt thereof, of the formula:

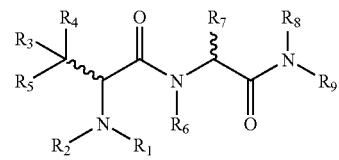

wherein:

$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is H or CH$_3$;

$R_7$ and $R_8$ are independently selected from the group consisting of: H, R, and ArR—;

and $R_9$ is:

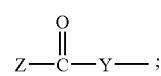

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

17. The compound of claim 14, wherein R$_6$ is H or CH$_3$.

18. The compound of claim 17, wherein R$_6$ is H.

19. A compound or pharmaceutically acceptable salt thereof, of the formula:

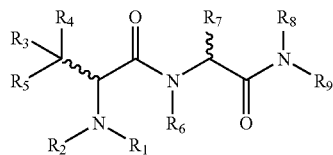

I wherein:

R$_1$ and R$_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;

R$_3$ and R$_4$ are independently selected from the group consisting of: H, R, and ArR—, or R$_3$ and R$_4$ are joined to form a ring;

R$_5$ is selected from the group consisting of: H, R, ArR—, and Ar;

R$_6$ is selected from the group consisting of: H, R, and ArR—;

R$_7$ is independently selected from the group consisting of: H, R, and ArR—;

R$_8$ is H or CH$_3$;

and

R$_9$ is:

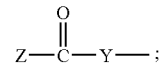

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

20. The compound of claim 14, wherein R$_8$ is H or CH$_3$.

21. The compound of claim 17, wherein R$_8$ is H or CH$_3$.

22. The compound of claim 21, wherein R$_8$ is CH$_3$.

23. A compound or pharmaceutically acceptable salt thereof, of the formula:

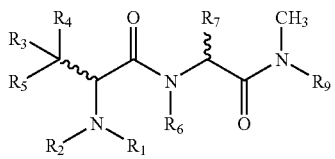

wherein:
$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;
$R_3$ and $R_4$ are independently selected from the group consisting of: H, R, and ArR—, or $R_3$ and $R_4$ are joined to form a ring;
$R_5$ is selected from the group consisting of: H, R, ArR—, and Ar;
$R_7$ is independently selected from the group consisting of: H, R, and ArR—;
and
$R_9$ is:

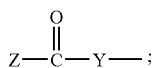

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{11}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group,
the ring formed by joining $R_1$ and $R_2$ or by joining $R_3$ and $R_4$ is a three to seven member non-aromatic cyclic skeleton within the definition of R,
Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;
X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;
Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and
Z is defined as a moiety selected from the group consisting of: —OH, —OR; —SH; —SR; —$NH_2$; —$NRCH(R_{11})$COOH; and —$NHCH(R_{11})$COOH, wherein $R_{11}$ is a moiety having the formula: R, or —$(CH_2)_n NR_{12}R_{13}$ wherein n=1-4 and $R_{12}$ and $R_{13}$ are independently selected from the group consisting of: H; R; and —C(NH)($NH_2$), or pharmaceutically acceptable salt thereof.

24. The compound of claim 14, wherein $R_6$ is H and $R_8$ is $CH_3$.

25. A compound or pharmaceutically acceptable salt thereof, of the formula:

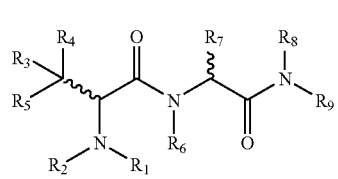

wherein:
$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;
$R_3$ and $R_4$ are independently selected from the group consisting of: H, R, and ArR—, or $R_3$ and $R_4$ are joined to form a ring;
$R_5$ is selected from the group consisting of: H, R, ArR—, and Ar;
$R_6$ is selected from the group consisting of: H, R, and ArR—;
$R_7$ is a three to six carbon atom, branched alkyl group;
$R_8$ is independently selected from the group consisting of: H, R, and ArR—;
and
$R_9$ is:

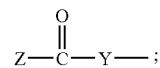

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group,
the ring formed by joining $R_1$ and $R_2$ or by joining $R_3$ and $R_4$ is a three to seven member non-aromatic cyclic skeleton within the definition of R,
Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;
X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —$NH_2$; —$NRCH(R_{11})$COOH; and —$NHCH(R_{11})COOH$, wherein $R_{11}$ is a moiety having the formula: R, or —$(CH_2)_nNR_{12}R_{13}$, wherein n=1-4 and $R_{12}$ and $R_{13}$ are independently selected from the group consisting of: H; R; and —$C(NH)(NH_2)$, or pharmaceutically acceptable salt thereof.

26. The compound of claim 14, wherein $R_7$ is a three to six carbon atom, branched alkyl group.

27. The compound of claim 17, wherein $R_7$ is a three to six carbon atom, branched alkyl group.

28. The compound of claim 21, wherein $R_7$ is a three to six carbon atom, branched alkyl group.

29. The compound of claim 25, wherein $R_7$ is —$C(CH_3)_3$.

30. A compound or pharmaceutically acceptable salt thereof, of the formula:

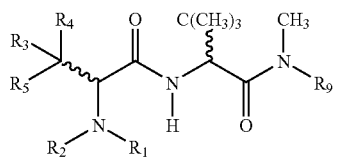

wherein:

$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

and $R_9$ is:

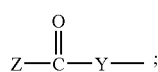

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —$O_2CR$, —SH, —SR, —SOCR, —$NH_2$, —NHR, —$N(R)_2$, —NHCOR, —NRCOR, —I, —Br, —Cl, —F, —CN, —$CO_2H$, —$CO_2R$, —CHO, —COR, —$CONH_2$, —CONHR, —$CON(R)_2$, —COSH, —COSR, —$NO_2$, —$SO_3H$, —SOR, and —$SO_2R$;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —$NH_2$; —$NRCH(R_{11})$COOH; and —$NHCH(R_{11})COOH$, wherein $R_{11}$ is a moiety having the formula: R, or —$(CH_2)_nNR_{12}R_{13}$, wherein n=1-4 and $R_{12}$ and $R_{13}$ are independently selected from the group consisting of: H; R; and —$C(NH)(NH_2)$, or pharmaceutically acceptable salt thereof.

31. A compound or pharmaceutically acceptable salt thereof, of the formula:

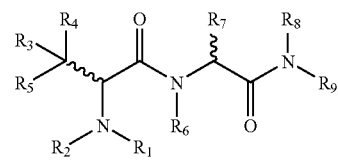

I wherein:

$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ is Y—COOH;

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —$OR_{10}$, —$O_2CR_{10}$, —SH, —$SR_{10}$, —$SOCR_{10}$, —$NH_2$, —$NHR_{10}$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, X is defined as a moiety selected from the group consisting of: —OH, —OR, ═O, ═S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X; and Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl.

32. A compound or pharmaceutically acceptable salt thereof, of the formula:

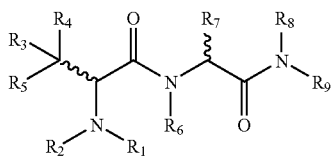

wherein:

$R_1$ and $R_2$ are independently selected from the group consisting of: H, R, and ArR—, provided that neither $R_1$ or $R_2$ is tert-butoxycarbonyl, and provided that if either one of $R_1$ and $R_2$ is H, each of $R_3$, $R_4$, $R_6$ and $R_8$ are H and $R_5$ is isopropyl or phenyl, and $R_7$ is methyl or benzyl, then for whichever of $R_1$ or $R_2$ is R or ArR—, the definition of R is limited to a saturated or unsaturated moiety having a linear, branched, or non-aromatic cyclic skeleton containing one to ten carbon atoms, zero to four nitrogen atoms, and zero to four sulfur atoms, and the carbon atoms are optionally substituted with: ═S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ has the formula:

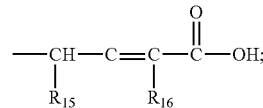

wherein $R_{15}$ is selected from the group consisting of methyl, ethyl, n-propyl, isopropyl, tert-butyl, iso-butyl, and sec-butyl; and $R_{16}$ is selected from the group consisting of H, methyl, ethyl, propyl, iso-propyl, n-butyl, iso-butyl and sec-butyl;

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: ═O, ═S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X; and X is defined as a moiety selected from the group consisting of: —OH, —OR, ═O, ═S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R.

33. A compound or pharmaceutically acceptable salt thereof, of the formula:

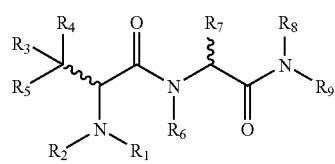

wherein:

$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ has the formula:

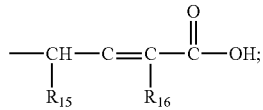

wherein $R_{15}$ is selected from the group consisting of methyl, ethyl, n-propyl, isopropyl, tert-butyl, iso-butyl, and sec-butyl; and $R_{16}$ is methyl;

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R; and Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X.

34. A compound or pharmaceutically acceptable salt thereof, of the formula:

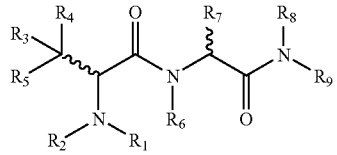

wherein:

$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ has the formula:

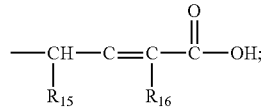

wherein $R_{15}$ is isopropyl and $R_{16}$ is methyl;

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R; and Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X.

35. A compound or pharmaceutically acceptable salt thereof, of the formula:

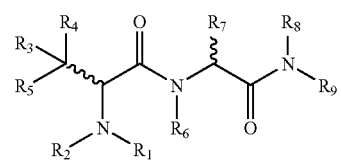

wherein:

$R_1$ and $R_2$ are independently selected from the group consisting of: H, R, and ArR—, provided that neither $R_1$ or $R_2$ is tert-butoxycarbonyl, or $R_1$ and $R_2$ are joined to form a ring;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is H or CH$_3$;

$R_7$ is a three to six carbon atom, branched alkyl group;

$R_8$ is independently selected from the group consisting of: H, R, and ArR—;

and $R_9$ has the formula:

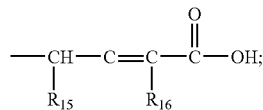

wherein $R_{15}$ is selected from the group consisting of: methyl, ethyl, n-propyl, isopropyl, tert-butyl, iso-butyl, and sec-butyl; and $R_{16}$ is selected from the group consisting of H, methyl, ethyl, propyl, iso-propyl, n-butyl, iso-butyl and sec-butyl R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R; and Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X.

36. A compound or pharmaceutically acceptable salt thereof, of the formula:

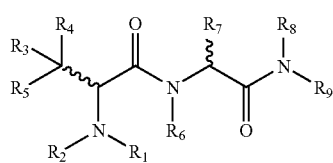

and having the configuration:

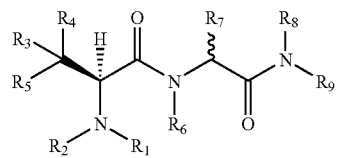

wherein:

$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;

$R_3$ and $R_4$ are independently selected from the group consisting of: H, R, and ArR—, or $R_3$ and $R_4$ are joined to form a ring;

$R_5$ is selected from the group consisting of: H, R, ArR—, and Ar;

$R_6$ is selected from the group consisting of: H, R, and ArR—;

$R_7$ and $R_8$ are independently selected from the group consisting of: H, R, and ArR—; and $R_9$ is:

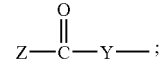

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein $R_{10}$ is a linear, branched or cyclic, one to ten carbon saturated or unsaturated alkyl group, the ring formed by joining $R_3$ and $R_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein $R_{11}$ is a moiety having the formula: R, or —(CH$_2$)$_n$NR$_{12}$R$_{13}$, wherein n=1-4 and $R_{12}$ and $R_{13}$ are independently selected from the group consisting of: H; R; and —C(NH)(NH$_2$), or pharmaceutically acceptable salt thereof.

37. A compound or pharmaceutically acceptable salt thereof, of the formula:

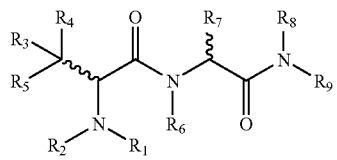

wherein:
$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;
$R_3$ and $R_4$ are independently selected from the group consisting of: H, R, and ArR—, or $R_3$ and $R_4$ are joined to form a ring;
$R_5$ is selected from the group consisting of: H, R, ArR—, and Ar;
$R_6$ is selected from the group consisting of: H, R, and ArR—;
$R_7$ and $R_8$ are independently selected from the group consisting of: H, R, and ArR—; and
$R_9$ is:

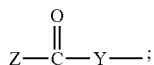

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{11}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group,
the ring formed by joining $R_3$ and $R_4$ is a three to seven member non-aromatic cyclic skeleton within the definition of R,
Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;
X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;
Y is a linear, unsaturated, two to six carbon alkyl group, optionally substituted with R, ArR—, or X; provided however if $R_8$ is H, then the optional substituents on Y are limited to R and ArR— wherein R is linear, branched or cyclic alkyl of one to ten carbon atoms and Ar is phenyl, naphthyl, anthracyl, or phenanthryl, wherein Y comprises a chiral center of the S-configuration and
Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

38. A compound or pharmaceutically acceptable salt thereof, of the formula:

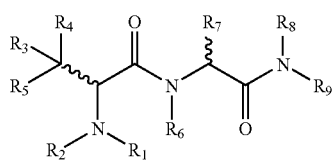

and having the configuration:

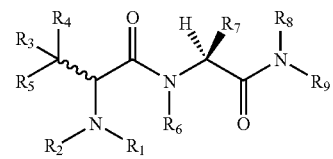

wherein:
$R_1$ and $R_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;
$R_3$ and $R_4$ are independently selected from the group consisting of: H, R, and ArR—, or $R_3$ and $R_4$ are joined to form a ring;
$R_5$ is selected from the group consisting of: H, R, ArR—, and Ar;
$R_6$ is selected from the group consisting of: H, R, and ArR—;
$R_7$ and $R_8$ are independently selected from the group consisting of: H, R, and ArR—; and
$R_9$ is:

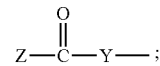

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{11}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R, Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof.

39. A compound or pharmaceutically acceptable salt thereof, of the configuration:

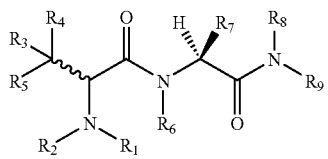

and having the formula:

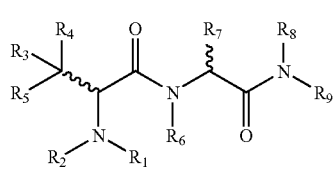

wherein R$_5$ is Ar; R$_3$ and R$_4$ are each CH$_3$; R$_1$, R$_2$, R$_6$ and R$_8$ are independently H or CH$_3$; R$_7$ is a three to six carbon branched alkyl group; and, R$_9$ has the formula

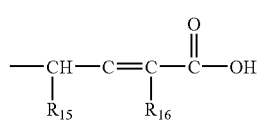

wherein R$_{15}$ is selected from the group consisting of methyl, ethyl, n-propyl, isopropyl, tert-butyl, iso-butyl, and sec-butyl; and R$_{16}$ is selected from the group consisting of H, methyl, ethyl, propyl, iso-propyl, n-butyl, iso-butyl and sec-butyl;

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_1$ and R$_2$ or by joining R$_3$ and R$_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X.

40. A compound or pharmaceutically acceptable salt thereof, of the formula:

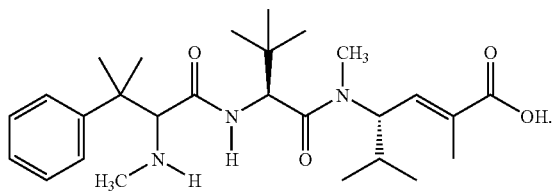

41. A pharmaceutical composition comprising a compound or pharmaceutically acceptable salt thereof, of the formula

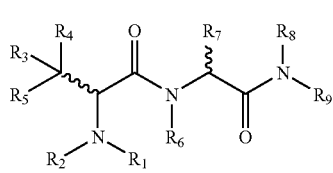

wherein:

R$_1$ and R$_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$;

R$_3$ and R$_4$ are independently selected from the group consisting of: H, R, and ArR—, or R$_3$ and R$_4$ are joined to form a ring;

R$_5$ is selected from the group consisting of: H, R, ArR—, and Ar;

R$_6$ is selected from the group consisting of: H, R, and ArR—;

R$_7$ and R$_8$ are independently selected from the group consisting of: H, R, and ArR—; and R$_9$ is:

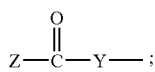

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_1$ and R$_2$ or by joining R$_3$ and R$_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

Y is a linear, unsaturated, two to six carbon alkyl group, optionally substituted with R, ArR—, or X; provided however if R$_8$ is H, then the optional substituents on Y are limited to R and ArR— wherein R is linear, branched or cyclic alkyl of one to ten carbon atoms and Ar is phenyl, naphthyl, anthracyl, or phenanthryl; and Z is defined as a moiety selected from the group consisting of: —OH, —OR; —SH; —SR; —NH$_2$; —NRCH(R$_{11}$)COOH; and —NHCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$), or pharmaceutically acceptable salt thereof; and an acceptable pharmaceutical excipient.

42. A method of inhibiting mitosis of a tumor cell comprising contacting the tumor cell with an effective amount of a compound according to claim 1.

43. A compound or pharmaceutically acceptable salt thereof, of the formula:

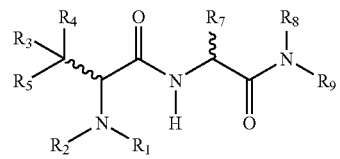

wherein:

R$_1$ and R$_2$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, and —NO$_2$;

R$_3$ and R$_4$ are H or a saturated or unsaturated moiety having a linear, branched, or non-aromatic cyclic alkyl containing one to ten carbon atoms optionally substituted with: =O, =S, —OH, —SH, —NH$_2$, —I, —Br, —Cl, —F, —CN, —CO$_2$H, —CHO, —CONH$_2$, —COSH, —NO$_2$, —SO$_3$H, or R$_3$ and R$_4$ are joined to form a ring;

R$_5$ is selected from the group consisting of: H, R, ArR—, and Ar;

R$_7$ is ArR— or a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —SH, —NH$_2$, —I, —Br, —Cl, —F, —CN, —CO$_2$H, —CHO, —CONH$_2$, —COSH, —NO$_2$;

R$_8$ is selected from the group consisting of: H and a saturated or unsaturated moiety having a linear, branched, or non-aromatic cyclic skeleton containing one to ten carbon atoms optionally substituted with —OH; and R$_9$ is:

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining R$_3$ and R$_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

Y is a linear, unsaturated, two to six carbon alkyl group, optionally substituted with:
(a) phenyl,
(b) naphthyl,
(c) anthracyl,
(d) phenanthryl, or
(e) a saturated or unsaturated moiety having a linear, branched, or non-aromatic cyclic skeleton consisting of one to ten carbon atoms optionally substituted with: =S, —OH; and Z is defined as a moiety selected from the group consisting of: —OH, —OR; —SH; —SR; —NH$_2$; or pharmaceutically acceptable salt thereof.

44. A compound or pharmaceutically acceptable salt thereof, of the formula:

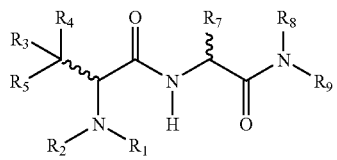

wherein:
$R_1$ and $R_2$ are independently selected from the group consisting of: H, methyl, ethyl, propyl and n-butyl;

$R_3$ and $R_4$ are independently selected from the group consisting of H, methyl, ethyl, n-propyl and n-butyl, or $R_3$ and $R_4$ are joined to form a three to seven member non-aromatic ring;

$R_5$ is selected from the group consisting of: R, ArR—, and Ar;

$R_7$ is ArR— or a saturated or unsaturated moiety having a linear, branched, or non-aromatic cyclic skeleton containing one to ten carbon atoms, zero to four oxygen atoms, and zero to four sulfur atoms, and the carbon atoms are optionally substituted with: =O, —OH, —SH, —NH$_2$, —I, —Br, —Cl, —F, —CN, —CO$_2$H, —CHO;

$R_8$ is selected from the group consisting of: H and CH$_3$; and $R_9$ is:

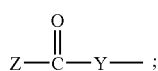

R is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NHR$_{10}$, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is a linear, branched or cyclic, one to ten carbon saturated or unsaturated alkyl group, the ring formed by joining $R_1$ and $R_2$ or by joining $R_3$ and $R_4$ is a three to seven member non-aromatic cyclic skeleton within the definition of R, X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Ar is an aromatic ring selected from the group consisting of: phenyl, naphthyl, anthracyl, phenanthryl, furyl, pyrrolyl, thiophenyl, benzofuryl, benzothiophenyl, quinolinyl, isoquinolyl, imidazolyl, thiazolyl, oxazolyl, and pyridinyl, optionally substituted with R or X;

Y is a linear, unsaturated, two to six carbon alkyl group, optionally substituted with phenyl, naphthyl, anthracyl, phenanthryl or a saturated or unsaturated moiety having a linear, branched, or non-aromatic cyclic skeleton containing one to ten carbon atoms optionally substituted with: =S, —OH; and Z is defined as a moiety selected from the group consisting of: —OH; —OR; —SH; —SR; —NH$_2$; or pharmaceutically acceptable salt thereof.

45. The compound of claim 43, of the configuration:

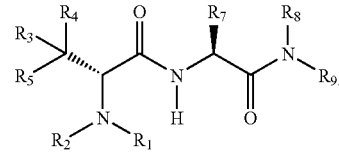

46. The compound of claim 43, of the configuration:

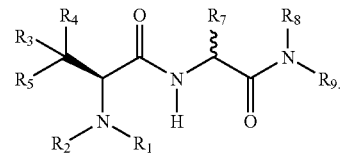

47. A method for treating colon cancer comprising administering to a patient in need thereof an anti-mitotic effective amount of a compound according to claim 1.

48. A method of treating breast cancer comprising administering to a patient in need thereof an anti-mitotic effective amount of a compound according to claim 1.

49. A method of treating lung cancer comprising administering to a patient in need thereof an anti-mitotic effective amount of a compound according to claim 1.

* * * * *

UNITED STATES PATENT AND TRADEMARK OFFICE
CERTIFICATE OF CORRECTION

PATENT NO. : 7,579,323 B1  Page 1 of 1
APPLICATION NO. : 09/581511
DATED : August 25, 2009
INVENTOR(S) : Raymond Andersen et al.

It is certified that error appears in the above-identified patent and that said Letters Patent is hereby corrected as shown below:

Title Page -

Item (22) PCT Filed, please correct to read as follows:

--(22) PCT Filed: December 18, 1998--

Signed and Sealed this

Second Day of February, 2010

David J. Kappos
*Director of the United States Patent and Trademark Office*